US011395681B2

(12) United States Patent
Luzzi et al.

(10) Patent No.: US 11,395,681 B2
(45) Date of Patent: Jul. 26, 2022

(54) RETENTION DEVICES, LATTICES AND RELATED SYSTEMS AND METHODS

(71) Applicant: WOVEN ORTHOPEDIC TECHNOLOGIES, LLC, Manchester, CT (US)

(72) Inventors: Robert Luzzi, Silverthorne, CO (US); Francis Patrick Magee, Mackay, ID (US)

(73) Assignee: WOVEN ORTHOPEDIC TECHNOLOGIES, LLC, Manchester, CT (US)

(*) Notice: Subject to any disclaimer, the term of this patent is extended or adjusted under 35 U.S.C. 154(b) by 40 days.

(21) Appl. No.: 15/836,659

(22) Filed: Dec. 8, 2017

(65) Prior Publication Data

US 2018/0325556 A1 Nov. 15, 2018

Related U.S. Application Data

(60) Provisional application No. 62/432,399, filed on Dec. 9, 2016.

(51) Int. Cl.
*A61B 17/68* (2006.01)
*A61B 17/86* (2006.01)
(Continued)

(52) U.S. Cl.
CPC .......... *A61B 17/686* (2013.01); *A61B 17/86* (2013.01); *A61F 2/30907* (2013.01);
(Continued)

(58) Field of Classification Search
CPC .................................................. A61B 17/686
See application file for complete search history.

(56) References Cited

U.S. PATENT DOCUMENTS

| 517,668 A | 4/1894 | Still |
| 1,486,527 A | 3/1924 | Larkin |

(Continued)

FOREIGN PATENT DOCUMENTS

| CN | 201046258 Y | 4/2008 |
| CN | 201073336 Y | 6/2008 |

(Continued)

OTHER PUBLICATIONS

NuVasive, Inc.; Patent Issued for Orthopedic Screw Insert, dated Feb. 23, 2015.

(Continued)

*Primary Examiner* — Rebecca S Preston
(74) *Attorney, Agent, or Firm* — Michele V. Frank; Venable LLP

(57) ABSTRACT

A woven retention device that is configured to receive a fastener in a bone hole can be configured to promote bone ingrowth and impede biofilm formation. The woven retention device can be made of woven filaments that outline apertures of varying sizes and shapes and can serve as an interface between the fastener and the bone material. In a first relaxed state, the interwoven filaments can outline apertures of varying sizes and shapes within a predetermined range and in a second constricted state inside the bone hole with the fastener the interwoven filaments can outline apertures of decreased area that still fall within the predetermined range. The woven retention device can be configured to allow for optimal bone growth while at the same time minimizing the likelihood that biofilm forms thereon.

21 Claims, 14 Drawing Sheets

(51) Int. Cl.
  *A61F 2/30* (2006.01)
  *A61B 17/00* (2006.01)
  *A61F 2/08* (2006.01)
(52) U.S. Cl.
  CPC .............. *A61B 2017/00526* (2013.01); *A61B 2017/8655* (2013.01); *A61F 2/08* (2013.01); *A61F 2002/30914* (2013.01); *A61F 2310/00023* (2013.01)

(56) References Cited

U.S. PATENT DOCUMENTS

| | | | |
|---|---|---|---|
| 1,516,652 A | 11/1924 | Tomkinson | |
| 1,517,668 A | 12/1924 | Still | |
| 2,148,164 A | 2/1939 | Krippendorf | |
| 2,326,453 A | 8/1943 | Gelpcke | |
| 2,388,693 A | 11/1945 | Jeckel | |
| 2,879,687 A | 3/1959 | Leimbach | |
| 2,936,670 A | 5/1960 | Walter | |
| 2,983,182 A | 5/1961 | Shobert | |
| 3,054,406 A | 9/1962 | Francis | |
| 3,187,752 A | 6/1965 | Glick | |
| 3,199,398 A | 8/1965 | Weisz | |
| 3,232,163 A | 2/1966 | George | |
| 3,363,502 A | 1/1968 | Florentine | |
| 3,371,573 A | 3/1968 | Koreki | |
| 3,710,789 A | 1/1973 | Ersek | |
| 3,714,862 A | 2/1973 | Berger | |
| 3,921,496 A | 11/1975 | Helderman | |
| 4,011,602 A | 3/1977 | Rybicki et al. | |
| 4,064,567 A | 12/1977 | Burstein et al. | |
| 4,158,984 A | 6/1979 | Griffiths | |
| 4,182,339 A | 1/1980 | Hardy, Jr. | |
| 4,205,399 A | 6/1980 | Shalaby et al. | |
| 4,304,169 A | 12/1981 | Cimprich et al. | |
| 4,383,527 A | 5/1983 | Asnis et al. | |
| 4,394,370 A | 7/1983 | Jefferies | |
| 4,409,974 A | 10/1983 | Freedland | |
| 4,453,539 A | 6/1984 | Raftopoulos et al. | |
| 4,520,821 A | 6/1985 | Schmidt et al. | |
| 4,563,489 A | 1/1986 | Urist | |
| 4,566,466 A | 1/1986 | Ripple et al. | |
| 4,567,917 A | 2/1986 | Millard | |
| 4,584,722 A | 4/1986 | Levy et al. | |
| 4,610,688 A | 9/1986 | Silvestrini et al. | |
| 4,640,271 A | 2/1987 | Lower | |
| 4,693,721 A | 9/1987 | Ducheyne | |
| 4,708,132 A | 11/1987 | Silvestrini | |
| 4,711,232 A | 12/1987 | Fischer et al. | |
| 4,716,807 A | 1/1988 | Fischer | |
| 4,716,893 A | 1/1988 | Fischer et al. | |
| 4,753,149 A | 6/1988 | Celani | |
| 4,760,843 A | 8/1988 | Fischer et al. | |
| 4,776,330 A | 10/1988 | Chapman et al. | |
| 4,777,860 A | 10/1988 | Bassett et al. | |
| 4,790,852 A | 12/1988 | Noiles | |
| 4,803,909 A | 2/1989 | Smith | |
| 4,870,957 A | 10/1989 | Goble et al. | |
| 4,894,063 A | 1/1990 | Nashef | |
| 4,913,028 A | 4/1990 | Yoshiya | |
| 4,917,700 A | 4/1990 | Aikins | |
| 5,013,318 A | 5/1991 | Spranza, III | |
| 5,041,114 A | 8/1991 | Chapman et al. | |
| 5,059,211 A | 10/1991 | Stack et al. | |
| 5,084,050 A | 1/1992 | Draenert | |
| 5,171,148 A | 12/1992 | Wasserman et al. | |
| 5,186,992 A | 2/1993 | Kite, III | |
| 5,211,647 A | 5/1993 | Schmieding | |
| 5,221,261 A | 6/1993 | Termin et al. | |
| 5,257,571 A | 11/1993 | Richardson | |
| 5,268,001 A | 12/1993 | Nicholson et al. | |
| 5,300,075 A | 4/1994 | Gordon | |
| 5,354,292 A | 10/1994 | Braeuer et al. | |
| 5,380,334 A | 1/1995 | Torrie et al. | |
| 5,383,387 A | 1/1995 | Chesterfield et al. | |
| 5,385,077 A | 1/1995 | Akiyama et al. | |
| 5,443,499 A | 8/1995 | Schmitt | |
| 5,456,721 A | 10/1995 | Legrand | |
| 5,458,601 A | 10/1995 | Young, Jr. et al. | |
| 5,490,750 A | 2/1996 | Gundy | |
| 5,501,133 A | 3/1996 | Brookstein et al. | |
| 5,520,084 A | 5/1996 | Chesterfield et al. | |
| 5,571,184 A | 11/1996 | DeSatnick | |
| 5,628,788 A | 5/1997 | Pinchuk | |
| 5,629,077 A | 5/1997 | Turnlund et al. | |
| 5,641,256 A | 6/1997 | Gundy | |
| 5,713,904 A | 2/1998 | Errico et al. | |
| 5,716,359 A | 2/1998 | Ojima et al. | |
| 5,718,159 A | 2/1998 | Thompson | |
| 5,725,541 A | 3/1998 | Anspach, III et al. | |
| 5,741,325 A | 4/1998 | Chaikof et al. | |
| 5,756,457 A | 5/1998 | Wang et al. | |
| 5,758,562 A | 6/1998 | Thompson | |
| 5,766,250 A | 6/1998 | Chervitz et al. | |
| 5,785,713 A | 7/1998 | Jobe | |
| D397,794 S | 9/1998 | Geber | |
| 5,849,013 A | 12/1998 | Whittaker et al. | |
| 5,871,504 A | 2/1999 | Eaton et al. | |
| 5,876,432 A | 3/1999 | Lau et al. | |
| 5,904,685 A | 5/1999 | Walawalkar | |
| 5,935,129 A | 8/1999 | McDevitt et al. | |
| 5,941,901 A | 8/1999 | Egan | |
| 5,957,974 A | 9/1999 | Thompson et al. | |
| 5,961,524 A | 10/1999 | Crombie | |
| 5,981,926 A | 11/1999 | Kim | |
| 5,984,926 A * | 11/1999 | Jones .................. | A61B 17/686 606/322 |
| 6,019,786 A | 2/2000 | Thompson | |
| 6,030,162 A | 2/2000 | Huebner | |
| 6,039,740 A | 3/2000 | Olerud | |
| 6,042,592 A | 3/2000 | Schmitt | |
| 6,056,751 A | 5/2000 | Fenton, Jr. | |
| 6,068,632 A | 5/2000 | Carchidi et al. | |
| 6,080,155 A | 6/2000 | Michelson | |
| 6,099,530 A | 8/2000 | Simonian et al. | |
| 6,126,663 A | 10/2000 | Hair | |
| 6,143,029 A | 11/2000 | Rippstein | |
| 6,231,606 B1 | 5/2001 | Graf et al. | |
| 6,241,757 B1 | 6/2001 | An et al. | |
| 6,264,676 B1 | 7/2001 | Gellman et al. | |
| 6,283,966 B1 | 9/2001 | Houfburg | |
| 6,314,856 B1 | 11/2001 | Keith et al. | |
| 6,319,255 B1 | 11/2001 | Grundei et al. | |
| 6,325,822 B1 | 12/2001 | Chouinard et al. | |
| 6,336,940 B1 | 1/2002 | Graf et al. | |
| 6,342,068 B1 | 1/2002 | Thompson | |
| 6,355,044 B1 | 3/2002 | Hair | |
| 6,375,662 B1 | 4/2002 | Schmitt | |
| 6,398,807 B1 | 6/2002 | Chouinard et al. | |
| 6,413,260 B1 | 7/2002 | Berrevoets et al. | |
| 6,436,142 B1 | 8/2002 | Paes et al. | |
| 6,450,770 B1 | 9/2002 | Wang et al. | |
| 6,495,227 B1 | 12/2002 | Cahuzac | |
| 6,500,203 B1 | 12/2002 | Thompson et al. | |
| 6,540,770 B1 | 4/2003 | Tornier et al. | |
| 6,544,281 B2 | 4/2003 | ElAttrache et al. | |
| 6,551,352 B2 | 4/2003 | Clerc et al. | |
| 6,562,046 B2 | 5/2003 | Sasso | |
| 6,582,461 B1 | 6/2003 | Burmeister et al. | |
| 6,616,694 B1 | 9/2003 | Hart | |
| 6,616,996 B1 | 9/2003 | Keith et al. | |
| 6,622,604 B1 | 9/2003 | Chouinard et al. | |
| 6,626,939 B1 * | 9/2003 | Burnside ............... | A61L 31/148 623/1.38 |
| 6,631,666 B2 | 10/2003 | Cahuzac | |
| 6,645,211 B2 | 11/2003 | Magana | |
| 6,652,571 B1 | 11/2003 | White et al. | |
| 6,669,706 B2 | 12/2003 | Schmitt et al. | |
| 6,685,738 B2 | 2/2004 | Chouinard et al. | |
| 6,746,483 B1 | 6/2004 | Bojarski et al. | |
| 6,767,350 B1 | 7/2004 | Lob | |
| 6,792,979 B2 | 9/2004 | Konya et al. | |
| 6,814,734 B2 | 11/2004 | Chappuis et al. | |
| 6,817,076 B1 | 11/2004 | Stephenson | |

(56) References Cited

U.S. PATENT DOCUMENTS

| | | |
|---|---|---|
| 6,827,743 B2 | 12/2004 | Eisermann et al. |
| 6,840,769 B2 | 1/2005 | Augthun et al. |
| 6,863,692 B2 | 3/2005 | Meulink |
| D503,802 S | 4/2005 | Bjarnason |
| 6,875,216 B2 | 4/2005 | Wolf |
| 6,908,466 B1 | 6/2005 | Bonutti et al. |
| 6,942,666 B2 | 9/2005 | Overaker et al. |
| 6,942,693 B2 | 9/2005 | Chouinard et al. |
| 6,991,647 B2 | 1/2006 | Jadhav |
| 7,004,967 B2 | 2/2006 | Chouinard et al. |
| 7,022,124 B2 | 4/2006 | Takei et al. |
| 7,052,513 B2 | 5/2006 | Thompson |
| 7,093,527 B2 | 8/2006 | Rapaport et al. |
| 7,101,183 B2 | 9/2006 | Augthun et al. |
| 7,141,074 B2 | 11/2006 | Fanger et al. |
| 7,144,413 B2 | 12/2006 | Wilford et al. |
| 7,213,495 B2 | 5/2007 | McCullagh et al. |
| 7,237,466 B2 | 7/2007 | Chen |
| 7,255,712 B1 | 8/2007 | Steinberg |
| 7,275,471 B2 | 10/2007 | Nishri et al. |
| 7,279,008 B2 | 10/2007 | Brown et al. |
| 7,309,355 B2 | 12/2007 | Donnelly et al. |
| 7,311,031 B2 | 12/2007 | McCullagh et al. |
| 7,341,592 B1 | 3/2008 | Walters et al. |
| 7,341,601 B2 | 3/2008 | Eisermann et al. |
| 7,344,559 B2 | 3/2008 | Gray et al. |
| 7,407,512 B2 | 8/2008 | Bojarski et al. |
| 7,435,254 B2 | 10/2008 | Chouinard et al. |
| 7,513,865 B2 | 4/2009 | Bourne et al. |
| 7,547,321 B2 | 6/2009 | Silvestri et al. |
| 7,569,058 B2 | 8/2009 | Zwirnmann |
| 7,572,283 B1 | 8/2009 | Meridew |
| 7,572,298 B2 | 8/2009 | Roller et al. |
| 7,582,108 B2 | 9/2009 | Hierlemann et al. |
| 7,637,949 B2 | 12/2009 | Hart |
| D612,499 S | 3/2010 | Ondracek et al. |
| 7,682,392 B2 | 3/2010 | Serhan et al. |
| 7,699,893 B2 | 4/2010 | Donnelly et al. |
| 7,731,750 B2 | 6/2010 | Bojarski et al. |
| 7,740,657 B2 | 6/2010 | Brown, Jr. et al. |
| 7,749,233 B2 | 7/2010 | Farr et al. |
| 7,758,642 B2 | 7/2010 | Bojarski et al. |
| 7,785,357 B2 | 8/2010 | Guan et al. |
| D626,648 S | 11/2010 | Ahlgren |
| 7,824,433 B2 | 11/2010 | Williams |
| 7,833,249 B2 | 11/2010 | Shaolian et al. |
| 7,846,162 B2 | 12/2010 | Nelson et al. |
| 7,892,203 B2 | 2/2011 | Lenker et al. |
| 7,896,901 B2 | 3/2011 | Whittaker |
| 7,938,853 B2 | 5/2011 | Chouinard et al. |
| 7,963,972 B2 | 6/2011 | Foerster et al. |
| 7,967,851 B2 | 6/2011 | Bickley et al. |
| 7,988,732 B2 | 8/2011 | Bojarski et al. |
| 8,052,720 B2 | 11/2011 | Kuester et al. |
| 8,100,969 B2 | 1/2012 | Hart |
| 8,114,079 B2 | 2/2012 | Haidukewych et al. |
| 8,114,141 B2 | 2/2012 | Appenzeller et al. |
| 8,128,626 B2 | 3/2012 | Justin |
| 8,142,415 B2 | 3/2012 | Warnock, Jr. et al. |
| 8,151,682 B2 | 4/2012 | Lilburn et al. |
| 8,162,998 B2 | 4/2012 | Schlienger et al. |
| 8,163,031 B2 | 4/2012 | Truckai et al. |
| 8,202,306 B2 | 6/2012 | Dreyfuss |
| 8,221,479 B2 | 7/2012 | Glazer et al. |
| 8,226,714 B2 | 7/2012 | Beck, Jr. et al. |
| 8,226,715 B2 | 7/2012 | Hwang et al. |
| 8,241,340 B2 | 8/2012 | Froehlich |
| 8,257,395 B2 | 9/2012 | Bhatnagar et al. |
| 8,298,262 B2 | 10/2012 | Stone et al. |
| 8,308,779 B2 | 11/2012 | Reiley |
| 8,317,799 B2 | 11/2012 | Schon et al. |
| 8,317,863 B2 | 11/2012 | Cauldwell et al. |
| 8,347,772 B2 | 1/2013 | Dow et al. |
| 8,353,941 B2 | 1/2013 | Fricker et al. |
| 8,361,078 B2 | 1/2013 | Beyar et al. |
| 8,366,711 B2 | 2/2013 | Rabiner et al. |
| 8,372,115 B2 | 2/2013 | Kohm et al. |
| 8,382,849 B2 | 2/2013 | Thomas |
| 8,414,635 B2 | 4/2013 | Hyodoh et al. |
| 8,419,780 B2 | 4/2013 | Bickley et al. |
| 8,420,113 B2 | 4/2013 | Zhao |
| 8,435,293 B2 | 5/2013 | Donnelly et al. |
| 8,443,706 B2 | 5/2013 | Egres, Jr. |
| 8,459,164 B2 | 6/2013 | Lilburn et al. |
| 8,493,705 B2 | 7/2013 | Lin et al. |
| 8,496,705 B2 | 7/2013 | Hart |
| 8,506,605 B2 | 8/2013 | Bickley et al. |
| 8,523,902 B2 | 9/2013 | Heaven et al. |
| 8,523,916 B2 | 9/2013 | Anderson et al. |
| 8,523,951 B2 | 9/2013 | Kania |
| 8,545,499 B2 | 10/2013 | Lozier et al. |
| 8,546,456 B2 | 10/2013 | Rose et al. |
| 8,546,546 B2 | 10/2013 | Nakano |
| 8,546,752 B2 | 10/2013 | Henion et al. |
| 8,568,413 B2 | 10/2013 | Mazur et al. |
| 8,585,762 B2 | 11/2013 | Hall |
| 8,591,582 B2 | 11/2013 | Anderson et al. |
| 8,617,185 B2 | 12/2013 | Bonutti et al. |
| 8,628,464 B2 | 1/2014 | Bourne et al. |
| 8,636,753 B2 | 1/2014 | Buevich et al. |
| 8,652,171 B2 | 2/2014 | Stone et al. |
| 8,663,296 B2 | 3/2014 | Williams |
| 8,663,672 B2 | 3/2014 | Manrique et al. |
| 8,671,815 B2 | 3/2014 | Hancock et al. |
| 8,677,874 B2 | 3/2014 | Lilburn et al. |
| 8,690,962 B2 | 4/2014 | Dignam et al. |
| 8,696,748 B2 | 4/2014 | Bojarski et al. |
| 8,709,055 B2 | 4/2014 | Beyar et al. |
| 8,721,519 B2 | 5/2014 | Sheu et al. |
| 8,747,469 B2 | 6/2014 | Wang et al. |
| 8,747,470 B2 | 6/2014 | Beck, Jr. et al. |
| 8,753,391 B2 | 6/2014 | Lu et al. |
| 8,770,081 B2 | 7/2014 | David et al. |
| 8,794,118 B2 | 8/2014 | Dow et al. |
| 8,821,090 B2 | 9/2014 | Gruber |
| 8,833,224 B2 | 9/2014 | Thompson et al. |
| 8,840,677 B2 | 9/2014 | Kale et al. |
| 8,857,304 B2 | 10/2014 | Govari et al. |
| 8,858,606 B2 | 10/2014 | Graf et al. |
| 8,870,877 B2 | 10/2014 | Koogle, Jr. |
| 8,910,554 B2 | 12/2014 | Kinugasa |
| D723,166 S | 2/2015 | Igaki et al. |
| 8,951,293 B2 | 2/2015 | Glazer et al. |
| 8,956,394 B1 | 2/2015 | McDonnell |
| 8,956,410 B2 | 2/2015 | Donnelly et al. |
| 8,992,537 B1 | 3/2015 | McDonnell |
| 9,011,440 B2 | 4/2015 | Schlienger et al. |
| 9,060,809 B2 | 6/2015 | Tipirneni et al. |
| D740,427 S | 10/2015 | McDonnell et al. |
| 9,388,517 B2 | 7/2016 | Lilburn et al. |
| 9,416,472 B2 | 8/2016 | Scherrible et al. |
| 9,532,806 B2 | 1/2017 | McDonnell |
| 9,585,695 B2 | 3/2017 | Jones et al. |
| 9,907,593 B2 | 3/2018 | McDonnell |
| 9,943,351 B2 | 4/2018 | McDonnell et al. |
| 2002/0055749 A1 | 5/2002 | Esnouf et al. |
| 2002/0083821 A1 | 7/2002 | Uchida |
| 2002/0143340 A1 | 10/2002 | Kaneko |
| 2002/0147454 A1 | 10/2002 | Neto |
| 2003/0036761 A1 | 2/2003 | Smothers et al. |
| 2003/0045880 A1 | 3/2003 | Michelson |
| 2004/0024456 A1 | 2/2004 | Brown, Jr. et al. |
| 2004/0068267 A1 | 4/2004 | Harvie et al. |
| 2004/0073214 A1 | 4/2004 | Mehdizadeh |
| 2004/0094024 A1 | 5/2004 | Kim |
| 2004/0133204 A1 | 7/2004 | Davies |
| 2004/0176767 A1 | 9/2004 | Bickley |
| 2004/0225359 A1* | 11/2004 | Bojarski ............ A61B 17/3431 623/16.11 |
| 2005/0015154 A1 | 1/2005 | Lindsey et al. |
| 2005/0070930 A1 | 3/2005 | Kammerer |
| 2005/0150370 A1 | 7/2005 | Nishri et al. |
| 2005/0216006 A1 | 9/2005 | Orbay et al. |
| 2005/0216012 A1 | 9/2005 | Willmen |

(56) References Cited

U.S. PATENT DOCUMENTS

| | | |
|---|---|---|
| 2005/0251143 A1 | 11/2005 | Dillard |
| 2005/0255230 A1 | 11/2005 | Clerc et al. |
| 2006/0089646 A1 | 4/2006 | Bonutti |
| 2006/0129148 A1 | 6/2006 | Simmons et al. |
| 2006/0140739 A1 | 6/2006 | Komine |
| 2007/0038221 A1 | 2/2007 | Fine et al. |
| 2007/0060923 A1 | 3/2007 | Dreyfuss |
| 2007/0093899 A1 | 4/2007 | Dutoit et al. |
| 2007/0118131 A1 | 5/2007 | Gooch |
| 2007/0118144 A1 | 5/2007 | Truckai et al. |
| 2007/0162018 A1 | 7/2007 | Jensen et al. |
| 2007/0191956 A1 | 8/2007 | Prewett et al. |
| 2007/0250114 A1 | 10/2007 | Drapeau |
| 2007/0270941 A1 | 11/2007 | Headley et al. |
| 2008/0027445 A1 | 1/2008 | Brown et al. |
| 2008/0051793 A1 | 2/2008 | Erickson et al. |
| 2008/0221623 A1 | 9/2008 | Gooch |
| 2008/0221624 A1 | 9/2008 | Gooch |
| 2008/0255560 A1 | 10/2008 | Myers et al. |
| 2008/0262630 A1 | 10/2008 | Fulmer et al. |
| 2008/0281430 A1 | 11/2008 | Kelman et al. |
| 2009/0024147 A1 | 1/2009 | Ralph et al. |
| 2009/0136898 A1 | 5/2009 | Kim |
| 2009/0192609 A1* | 7/2009 | Klabunde ............ A61F 2/30907 623/16.11 |
| 2009/0193961 A1 | 8/2009 | Jensen et al. |
| 2009/0216338 A1 | 8/2009 | Gingras et al. |
| 2009/0254124 A1 | 10/2009 | Bickley et al. |
| 2009/0275974 A1* | 11/2009 | Marchand ........ A61B 17/12022 606/194 |
| 2009/0279980 A1 | 11/2009 | Gruber |
| 2009/0306777 A1 | 12/2009 | Widmer et al. |
| 2010/0015286 A1 | 1/2010 | Ghodsian et al. |
| 2010/0016940 A1 | 1/2010 | Shokoohi et al. |
| 2010/0042293 A1 | 2/2010 | Moshchuk et al. |
| 2010/0076503 A1 | 3/2010 | Beyar et al. |
| 2010/0125273 A1 | 5/2010 | Schwieger et al. |
| 2010/0152786 A1 | 6/2010 | Behrbalk |
| 2010/0168505 A1 | 7/2010 | Inman et al. |
| 2010/0179591 A1 | 7/2010 | Saltzman et al. |
| 2010/0185244 A1 | 7/2010 | Gooch |
| 2010/0292738 A1 | 11/2010 | Reiley |
| 2010/0318085 A1 | 12/2010 | Austin et al. |
| 2010/0324607 A1 | 12/2010 | Davis |
| 2010/0331881 A1 | 12/2010 | Hart |
| 2011/0061519 A1 | 3/2011 | Fields |
| 2011/0106177 A1 | 5/2011 | Lewis |
| 2011/0144766 A1 | 6/2011 | Kale et al. |
| 2011/0184472 A1 | 7/2011 | Niederberger et al. |
| 2011/0213467 A1 | 9/2011 | Lozier et al. |
| 2011/0230948 A1 | 9/2011 | Ehrenreich et al. |
| 2011/0238069 A1 | 9/2011 | Zajac et al. |
| 2012/0046698 A1 | 2/2012 | Kolb et al. |
| 2012/0065649 A1 | 3/2012 | Towler |
| 2012/0123416 A1 | 5/2012 | Gelfand et al. |
| 2012/0172934 A1 | 7/2012 | Fisher et al. |
| 2012/0239145 A1 | 9/2012 | Peterson et al. |
| 2012/0245704 A1 | 9/2012 | Childs |
| 2012/0259372 A1 | 10/2012 | Glazer et al. |
| 2012/0264084 A1 | 10/2012 | Hansson et al. |
| 2012/0330360 A1 | 12/2012 | Nishida |
| 2013/0013065 A1 | 1/2013 | Bills |
| 2013/0014544 A1 | 1/2013 | Winkler |
| 2013/0018318 A1 | 1/2013 | Ravichandran et al. |
| 2013/0103166 A1 | 4/2013 | Butler et al. |
| 2013/0131684 A1 | 5/2013 | Farrell |
| 2013/0178946 A1 | 7/2013 | Monaghan et al. |
| 2013/0184819 A1 | 7/2013 | Donnelly et al. |
| 2013/0226204 A1 | 8/2013 | Kumar |
| 2013/0289621 A1 | 10/2013 | Fulmer et al. |
| 2014/0046454 A1 | 2/2014 | Rose et al. |
| 2014/0052178 A1 | 2/2014 | Dooney, Jr. |
| 2014/0090549 A1 | 4/2014 | Hurlen |
| 2014/0094805 A1 | 4/2014 | Bonutti et al. |
| 2014/0094860 A1 | 4/2014 | Reimels |
| 2014/0100590 A1 | 4/2014 | Gingras et al. |
| 2014/0128916 A1 | 5/2014 | Williams |
| 2014/0135906 A1 | 5/2014 | Winner et al. |
| 2014/0171946 A1 | 6/2014 | Benson et al. |
| 2014/0194938 A1 | 7/2014 | Bojarski et al. |
| 2014/0207145 A1 | 7/2014 | Sennett |
| 2014/0243978 A1 | 8/2014 | Beck, Jr. et al. |
| 2014/0277150 A1 | 9/2014 | Jones et al. |
| 2014/0277449 A1 | 9/2014 | Jones |
| 2014/0358145 A1 | 12/2014 | Schaller et al. |
| 2015/0018878 A1 | 1/2015 | Rizk et al. |
| 2015/0045831 A1 | 2/2015 | Allen |
| 2015/0119984 A1 | 4/2015 | Donnelly et al. |
| 2015/0148883 A1 | 5/2015 | Hyodoh et al. |
| 2015/0238205 A1 | 8/2015 | Reiley |
| 2015/0275408 A1 | 10/2015 | Tahara et al. |
| 2015/0313720 A1 | 11/2015 | Lorio |
| 2015/0342764 A1 | 12/2015 | Ramzipoor et al. |
| 2016/0010248 A1 | 1/2016 | Lariviere et al. |
| 2016/0038187 A1 | 2/2016 | McDonnell |
| 2016/0038206 A1 | 2/2016 | McDonnell |
| 2016/0058524 A1 | 3/2016 | Tehrani et al. |
| 2016/0074071 A1 | 3/2016 | McDonnell et al. |
| 2016/0074072 A1 | 3/2016 | McDonnell et al. |
| 2016/0074084 A1 | 3/2016 | McDonnell et al. |
| 2016/0168769 A1 | 6/2016 | McDonnell |
| 2016/0183942 A1 | 6/2016 | Allen |
| 2016/0206452 A1* | 7/2016 | Berez ...................... A61F 2/966 |
| 2016/0317332 A1 | 11/2016 | Lilburn et al. |
| 2016/0345676 A1 | 12/2016 | Bruce et al. |
| 2017/0035481 A1 | 2/2017 | Magee et al. |
| 2017/0035482 A1 | 2/2017 | Magee et al. |
| 2017/0071634 A1 | 3/2017 | McDonnell |
| 2017/0128100 A1 | 5/2017 | Jones et al. |
| 2017/0165077 A1 | 6/2017 | McDonnell |
| 2017/0215934 A1 | 8/2017 | McDonnell |

FOREIGN PATENT DOCUMENTS

| | | |
|---|---|---|
| DE | 2414635 A1 | 10/1975 |
| EP | 0409364 A2 | 1/1991 |
| EP | 1614402 A1 | 1/2006 |
| FR | 2691626 A1 | 12/1993 |
| FR | 2725615 A1 | 4/1996 |
| FR | 2955259 A1 | 7/2011 |
| GB | 2 307 179 A | 5/1997 |
| JP | 10043199 A | 2/1998 |
| WO | 1983/002555 A1 | 8/1983 |
| WO | 1989/001320 A1 | 2/1989 |
| WO | 1994/007425 A1 | 4/1994 |
| WO | 1996/003084 A1 | 2/1996 |
| WO | 2001/056506 A1 | 8/2001 |
| WO | 2001/070135 A2 | 9/2001 |
| WO | 2006/105935 A1 | 10/2006 |
| WO | 2007/103404 A2 | 9/2007 |
| WO | 2010/042293 A1 | 4/2010 |
| WO | 2012024806 A1 | 3/2012 |
| WO | 2012/116319 A2 | 8/2012 |
| WO | 2012/121726 A1 | 9/2012 |
| WO | 2013/004763 A1 | 1/2013 |
| WO | 2013186525 A1 | 12/2013 |
| WO | 2015097416 A1 | 7/2015 |
| WO | 2016/022491 A1 | 2/2016 |
| WO | 2016/044471 A1 | 3/2016 |
| WO | 2017/024277 A1 | 2/2017 |
| WO | 2017/024280 A1 | 2/2017 |

OTHER PUBLICATIONS

Brown et al., "Intratunnel Tibial Fixation of Soft-Tissue Anterior Cruciate Ligament Grafts: Graft Sleeve and Tapered Screw," Clinical Gate, Nov. 14, 2015.

Camlog, "Surgical Procedure with the Camlog Screw-Line Implant," Nov. 17, 2015.

Arthrex, "The Next Generation in Foot and Ankle Repair and Reconstruction Technology," 2011.

(56) References Cited

OTHER PUBLICATIONS

Pechon et al., "Salvaging the Pullout Strength of Stripped Screws in Osteoporotic Bone," Geriatric Orthopaedic Surgery & Rehabilitation 4 (2); 50-52; Jun. 30, 2013.
Aga et al., "Biomechanical comparison of interference screws and combination screw and sheath devices for soft tissue anterior cruciate ligament reconstruction on the tibial side," The American Journal of Sports Medicine (41) 4; Feb. 4, 12, 2013.
Notice of Allowance issued in related Design U.S. Appl. No. 29/524,091 dated Jan. 25, 2016 [Available in IFW].
Supplementary European Search Report in corresponding European U.S. Appl. No. 15829032.0, dated Aug. 10, 2018.
ACE Surgical Supply Co., Inc. Titanium Augmentation Micro Mesh—7, http://www.acesurgical.com/bone-grafting/graft-holding-mesh-foils/mic . . . , Jun. 19, 2014.
Alves et al., "Injectability Evaluation of Tricalcium Phosphate Bone Cement", J Mater Sci Mater Med., vol. 19(5), 2008 (Abstract).
Andre Weimann, M.D., et al., Primary Stability of Bone-Patellar Tendon-Bone Graft Fixation With Biodegradable Pins, Arthroscopy: The Journal of Arthroscopic and Related Surgery, vol. 19, No. 10, Dec. 2003, pp. 1097-1102.
Biomesh® Neurological Patches N3L—Spinal dura-mater substitutes—Cousin Biotech, <http://www.cousin-biotech.com/uk/produit.php?idrubrique=16&idspecialite=35&idproduit=81>.
Bioretec—ActivaScrew Cannulated—Surgical Technique, <http://www.bioretec.com/products/pro_orthotrauma/activascrew-cannulated/surgical-technique.php>.
ConMed, Fixation Implants, <http://www.conmed.com/products/knee-fixation.php>.
D. S. Muckle et al., Biological Response to Woven Carbon Fibre Pads in the Knee, The Journal of Bone and Joint Surgery, 1989, 7I-B, pp. 60-62.
GORE-TEX® Soft Tissue Patch, <http://www.goremedical.com/stp/>.
Ho Jung Kang et al., An Experimental Intraarticular Implantation of Woven Carbon Fiber Pad into Osteochondral Defect of the Femoral Condyle in Rabbit, Yonsei Medical Journal, vol. 32, No. 2, 1991, pp. 108-116.
K.P. Chellamani et al., Medical textiles using Braiding Technology, Journal of Academia and Industrial Research (JAIR), vol. 2, Issue 1, Jun. 2013, pp. 21-26.
Maureen Suchenski, M.D. et al., Material Properties and Composition of Soft-Tissue Fixation, Arthroscopy: The Journal of Arthroscopic and Related Surgery, vol. 26, No. 6, Jun. 2010, pp. 821-831.
Medtronic Sofamor Danek, Vertex® Max, Reconstruction System Surgical Technique, © 2005.
Stephanie C. Von Plocki, et al., Biodegradable Sleeves for Metal Implants to Prevent Implant-Associated Infection: An Experimental In Vivo Study in Sheep, Veterinary Surgery, vol. 41, Issue 3, Apr. 2012, pp. 410-421.
Synthes GmbH, Angular Stable Locking System (ASLS). For angular stable locking of intra-medullary nails, Technique Guide, © Oct. 2008.
Synthes GmbH, DLS Dynamic Locking Screw. Combined with LCP Locking Compression Plate, Instructions for Use, © Oct. 2012.
Takanobu Nishizuka et al., Intramedullary-fixation Technique for Long Bone Fragility Fractures Using Bioabsorbable Materials, Orthopedic Research Annual Meeting, Mar. 2014.
The Open Prosthetics Project: suspension, <http://openprosthetics.org/suspension>.
VICRYL® (polyglactin 910) Woven Mesh—Ethicon, <http://www.ethicon.com/healthcare-professionals/products/tissue-hernia/mesh/vicryl-polyglactin-910-woven-mesh>.
International Search Report and Written Opinion in corresponding International Application No. PCT/US2015/065028, dated Feb. 12, 2016.
International Search Report and Written Opinion in International Application No. PCT/US15/50483, dated Dec. 28, 2015.
International Search Report and Written Opinion in International Application No. PCT/US2015/050506, dated Dec. 14, 2015.
International Search Report and Written Opinion in International Application No. PCT/US2015/043471, dated Nov. 3, 2015.
International Search Report and Written Opinion in International Application No. PCT/US2016/045899, dated Oct. 11, 2016.
International Search Report and Written Opinion in International Application No. PCT/US2016/045903, dated Nov. 2, 2016.
McDonnell et al.; Design U.S. Appl. No. 29/524,091, filed Apr. 16, 2015.
U.S. Appl. No. 29/524,091: Office Action dated Jun. 5, 2015.
U.S. Appl. No. 29/524,091: Notice of Allowance dated Jan. 25, 2016.
Non-Final Office Action issued in corresponding U.S. Appl. No. 14/209,514 dated Jul. 27, 2017 (10 pages).
Non-Final Office Action issued in corresponding U.S. Appl. No. 14/569,541 dated Feb. 27, 2017 (21 pages).
Non-Final Office Action issued in corresponding U.S. Appl. No. 14/487,895 dated Mar. 24, 2017 (6 pages).
Non-Final Office Action issued in corresponding U.S. Appl. No. 14/487,951 dated Mar. 22, 2017 (6 pages).
Non-Final Office Action issued in corresponding U.S. Appl. No. 15/359,021 dated Feb. 1, 2017 (16 pages).
Notice of Allowance issued in corresponding U.S. Appl. No. 15/359,021 dated Sep. 13, 2017 (8 pages).
International Search Report and Written Opinion in International Application No. PCT/US2017/065450, dated Mar. 3, 2018.
Notice of Allowance issued in related U.S. Appl. No. 15/804,645 dated Nov. 1, 2019 [Available in IFW].
Notice of Allowance issued in related U.S. Appl. No. 15/230,198 dated Oct. 2, 2019 [Available in IFW].
Office Action issued in related European Patent Application No. 15829032.0 dated Nov. 7, 2019.
Communication Pursuant to Article 94(3) EPC dated Feb. 3, 2022, directed to EP Application No. 17878127.4; 5 pages.

* cited by examiner

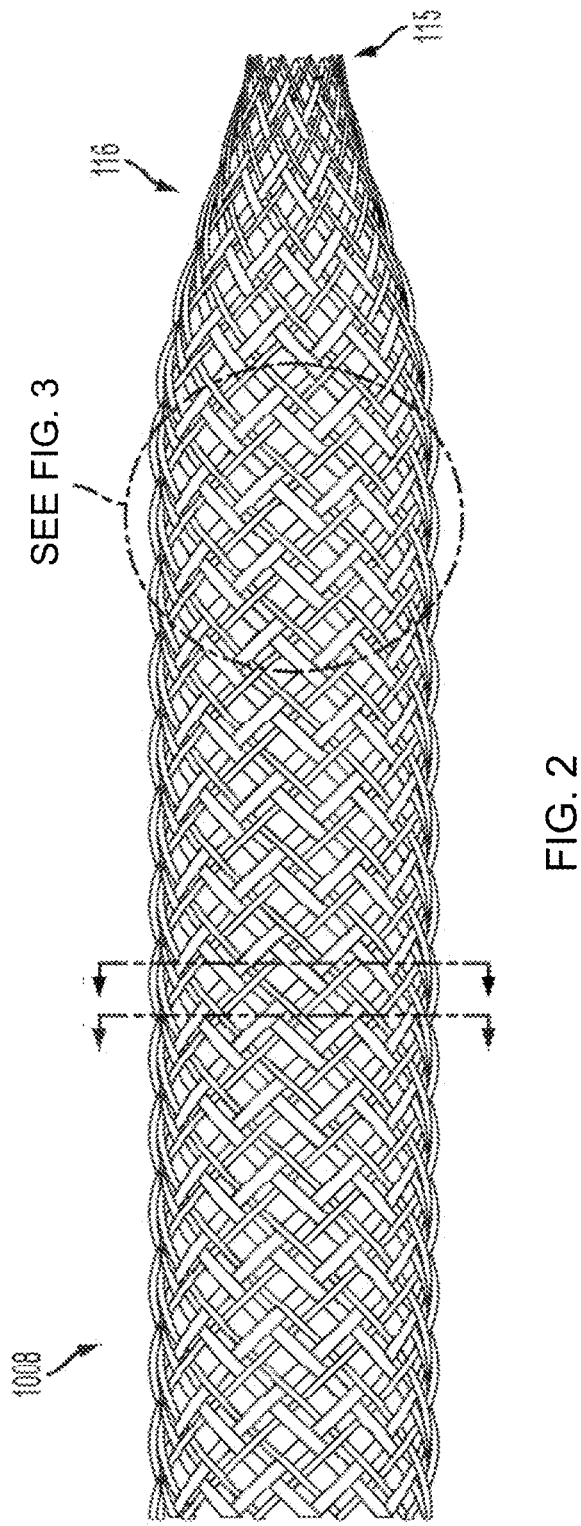

FIG. 12A  Small

FIG. 12B  Medium

FIG. 12C  Large

RETENTION DEVICES, LATTICES AND RELATED SYSTEMS AND METHODS

CROSS REFERENCE TO RELATED APPLICATION

This application claims priority to U.S. Provisional Application No. 62/432,399, filed Dec. 9, 2016, the contents of which is hereby incorporated herein by reference in its entirety.

TECHNICAL FIELD

The present invention relates to devices, systems and methods for use in fixing fasteners to bone tissue. Specifically, the present invention relates to maintaining a pore size within a predetermined range regardless of the diameter of the device.

BACKGROUND

In orthopedic surgery it is common to secure a bone screw to a patient's bone. Bone fracture repair is surgery to fix a broken bone using plates, nails, screws, or pins. It is common in the treatment of fractures to attach a plate to the bone utilizing bone screws. The resulting construct prevents motion of the fractured bone so that the bone can heal. Alternatively, one or more screws may be inserted across the break to hold it in place.

In the treatment of spinal disorders, pedicle screws are inserted into the patient's vertebrae to serve as anchor points that can then be connected with a rod. This construct prevents motion of the vertebral segments that are to be fused.

In the treatment of detached tendons, screw-like tissue anchors are inserted into the patient's bone to serve as an anchor for the reattachment of the tendon.

One complication with the use of bone screws is the loss of fixation or grip between the bone screw and the patient's bone. Another complication with the use of bone screws is the stripping of the hole in the bone when the bone screw is inserted. This results in the loss of purchase and holding strength of the bone screw.

The presence of osteoporotic bone or other disease states that weaken bone can increase the likelihood of complications by reducing the purchase or grip of the bone screw to the patient's bone, resulting in a loss of holding strength and loosening of the bone screw or pullout of the bone screw.

Infections deep inside bone require systemic antibacterial treatments, which disrupt entire systems.

Cellular responses and micro-organisms that create biofilms and the growth of soft tissues prevent bony ingrowth. Materials and conditions conducive for bony ingrowth may prevent the proliferation of biofilms or soft tissue in place of bone where bone is preferred for fixation and stability. Such conditions may include the space for ingrowth as bone cells perform some space, but not an infinite amount of space. This space may be the linear distance in 3-dimensions between obstructions.

A woven patch can be used in orthopedics. Currently, commercial applications use mesh, for example, to secure the lower, tibial end of a soft tissue ACL graft. In this sleeve, as described in the GTS Sleeve document, two of the lumens hold graft tissue and the third lumen accepts the GTS tapered fixation screw. See GTS Sleeve document. Another commercial application, such as the Opti-mesh™ 3-D deployable mesh pouch (Spineology, Inc.), is used in the vertebral body by containing bone material and restoring the height of vertebrae. There are other fiber or suture-based technologies that are not woven but function as a patch or shield. For example, pedicle shields have also been used with a semi-circular surface that are implanted within the pedicle to protect the spinal canal.

There remains a need for solutions to secure bone screws and facilitate bone healing through woven devices, materials and/or patches.

SUMMARY

A woven retention device to promote bone ingrowth and impede biofilm formation can include a sleeve body comprising a plurality of interwoven filaments; a proximal end that is proximal to the sleeve body and that is configured to receive a fastener; and a distal end that is distal to the sleeve body on an opposing side of the proximal end, wherein in a relaxed state of the woven retention device, the interwoven filaments outline pores, each of the pores having a pore size along a plane of the tubular lattice, each pore size within a range of 200-1000 µm, wherein in a constricted state of the woven retention device, the pore size changes as a function of a diameter of the sleeve body, the pore size remaining within the range of 200-1000 µm, and wherein the pores are configured to promote bone ingrowth.

An area of the pores can change dynamically by interwoven filaments translating with respect to each other without substantial deforming of the interwoven filaments.

The area of the pores can change by a function of a braid of the filaments.

The pore size can be defined along a long axis or a major axis of the sleeve body.

The interwoven filaments can define a plurality of protuberances distributed on an interior surface and an exterior surface of the tubular lattice at a predetermined spatial relationship.

In the relaxed state each pore can be shaped as one of a diamond, a rectangle, a square, or a parallelogram.

A woven retention device to promote bone growth can include a sleeve body comprising a plurality of interwoven filaments that form a substantially tubular lattice having a plurality of pores having a predetermined pore size, the plurality of pores defined by a plurality of adjacent filaments of the plurality of interwoven filaments, wherein the woven retention device is configured to move between a relaxed state and a constricted state, wherein the pore size falls within a predetermined range and remains substantially within the predetermined range when the woven retention device is in the relaxed state and the constricted state, and wherein the pore size promotes bone growth in the pores.

The pore size can be defined by a 3-dimensional distance between surfaces of the plurality of adjacent filaments.

The pores can define a parallelepiped between the plurality of adjacent filaments.

The 3-dimensional distance between surfaces of the plurality of adjacent filaments is a length between opposing diagonal corners of the pores.

The pore size can be within the range of 200 µm and 1000 µm.

The pore size can be about 600 µm.

The pore size can be defined when the woven retention device is in the relaxed state.

A plurality of protuberances can be distributed on an interior surface and an exterior surface of the tubular lattice at a predetermined spatial relationship.

The pore size can be defined along a long axis or a major axis of the sleeve body.

The pore size can remain in the range of 200 μm and 1000 μm when a diameter of the sleeve body changes.

A kit can include a first woven retention device having a first diameter, the first woven retention device having a first sleeve body comprising a first plurality of interwoven filaments that form a substantially tubular lattice having a plurality of first pores; and a second woven retention device having a second diameter, the second woven retention device having a second sleeve body comprising a second plurality of interwoven filaments that form a substantially tubular lattice having a plurality of second pores, wherein the second diameter is greater than the first diameter, and wherein the first pores and the second pores have substantially the same pore size, and wherein the pore size is within the range of 200 μm and 1000 μm.

The woven retention device can be configured to move between a relaxed state and a constricted state, and wherein the pore size remains substantially within the range when the woven retention device is in the relaxed state and the constricted state.

The kit can include a third woven retention device having a third diameter, the third woven retention device having a third sleeve body comprising a third plurality of interwoven filaments that form a substantially tubular lattice having a plurality of third pores, wherein, the third diameter is greater than the second diameter, and wherein a pore size of the third pores is substantially the same as the pore size of the first pores and the pore size of the second pores.

The first pores, the second pores, and the third pores can be defined by a 3-dimensional distance between surfaces of adjacent interwoven filaments of the respective plurality of interwoven filaments.

BRIEF DESCRIPTION OF DRAWINGS

FIG. 2 shows an implantable retention device with a tapered end along its longitudinal axis, according to an embodiment of the present invention.

FIG. 12a shows a small diameter woven retention device, according to embodiments of the present invention.

FIG. 12b shows a medium diameter woven retention device, according to embodiments of the present invention.

FIG. 12c shows a large diameter woven retention device, according to embodiments of the present invention.

Figure 1A:
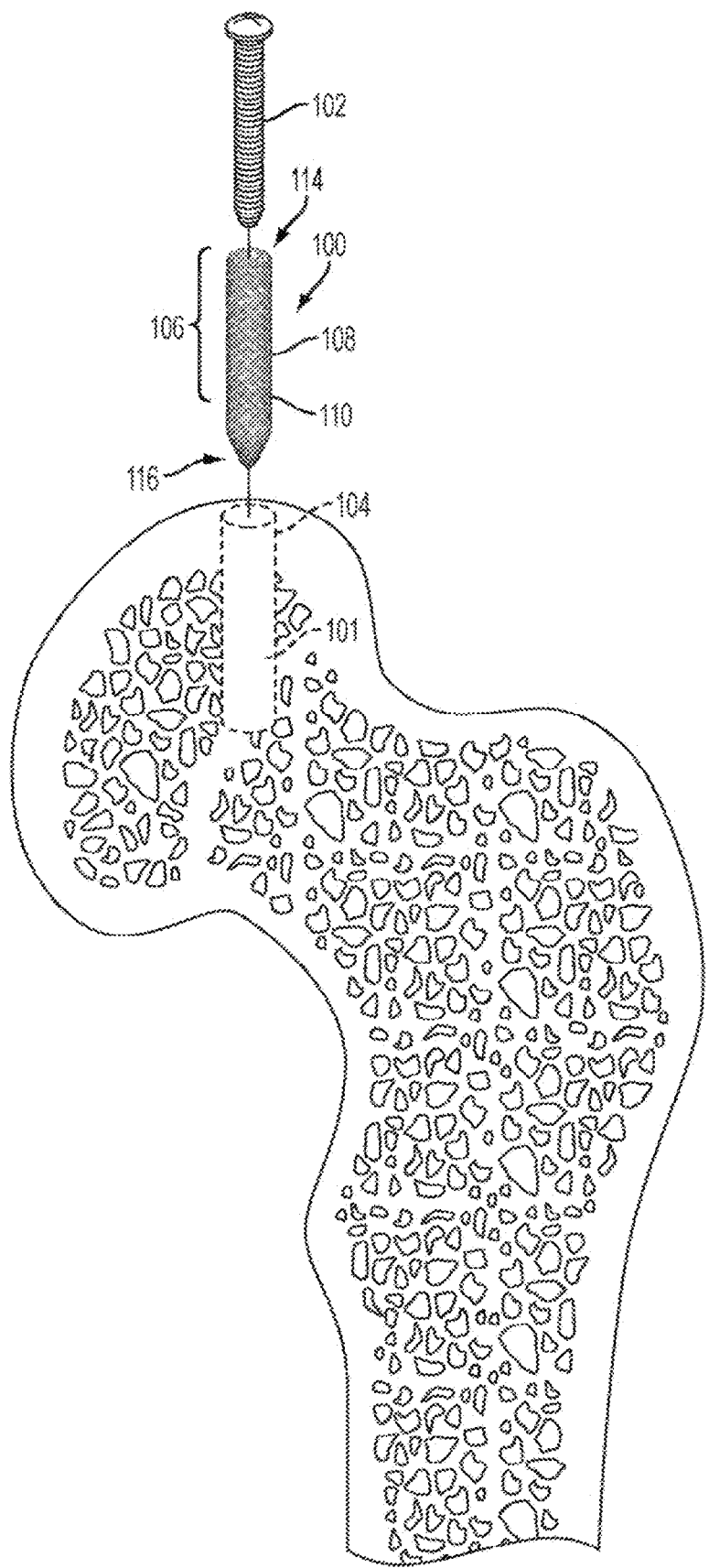
FIG. 1A shows a perspective view of a screw, an implantable retention device and a bone, according to an embodiment of the present invention.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The devices, systems and methods described herein may be used in the area of orthopedics and, in particular, orthopedic repairs. These include various devices, systems and methods directed to fixing and/or retaining fasteners in orthopedic applications. Fixing or retaining fasteners to bone tissue is complicated by the underlining bone tissue. Understanding that an underlying cause of failure with internal fixation in bone tissue is the bone, the devices, systems and methods described herein provide for solutions that address the implant site. At the implant site, the hole and the bone benefit from an enhanced interface.

The fixation and/or retention devices, systems and methods described herein maximize fixation and/or retention in the bone tissue, including, osteoporotic bone, bone of a poor quality, and mechanically poor bone in addition to healthy bone tissue. The fixation and/or retention devices, systems and methods described herein may be used with any type of fixation including, any types of screws, pins or fasteners.

The devices, systems and methods described herein enhance the interaction of a fastener, such as a bone anchor, to a bone hole to provide enhanced fixation. Additionally, the devices, systems and methods may repair the surface of the bone hole following damage to the bone hole as in the case of stripping of the hole in the bone when a bone screw is over-tightened. Also, the devices, systems and methods provide for an enhanced bone hole surface for the reattachment of tendons in, for example, anterior/posterior cruciate ligament repair procedures, rotator cuff repair procedures, etc. The devices enhance the surface of a bone hole to enhance fixation of a bone anchor to bone and permits bone ingrowth into its structure. The devices enhance the interaction between the surface of a bone hole and the fixation device. The devices interdigitate with the bony structure and interact with the fixation device. The device alone, as a single device, enhances the surface of a bone hole to enhance fixation of a bone anchor to bone and accommodates variations in the diameter and depth of the bone hole. The devices, systems and methods can enhance fixation without requiring the use of cement and/or adhesives.

The retention devices, lattices, fixation sleeves and/or patches, systems and methods described herein maximize fixation and/or retention in the bone tissue, including, osteoporotic bone, bone of a poor quality, and mechanically poor bone in addition to healthy bone tissue. The fixation sleeve and/or patches, systems and methods described herein may be used with any type of fixation including, any types of screws, pins, or fasteners.

The devices, systems and methods described herein can support a bone structure. In one embodiment, the devices, systems and methods can enhance the interaction of a bone anchor, such as a screw, a nail or a bone dowel, to a bone hole to provide enhanced fixation. Additionally, the devices, systems and methods may repair the exterior or interior surface of the bone following damage to the bone as in the case of stripping of the bone when a bone screw is over-tightened. Also, the devices, systems and methods provide for an enhanced bone surface for the reattachment of tendons in, for example, anterior/posterior cruciate ligament repair procedures, rotator cuff repair procedures, etc. The devices can enhance the surface of a bone to enhance fixation of a bone anchor to bone and can permit bone ingrowth into its structure. In another embodiment, the bone ingrowth can be enhanced with a coating of biological additive that actively promotes bone growth. The devices can enhance the interaction between the surface of the bone and the fixation device. The devices can interdigitate with the bony structure and interact with the fixation device. The device alone, as a single device, enhances the surface of a bone hole to enhance fixation of a bone anchor to bone and accommodates variations in the diameter and depth of the bone hole. In one embodiment, the devices, systems and methods can enhance fixation without requiring the use of cement and/or adhesives. In another embodiment, bone void filler such as cement can be applied to the surface of the bone and the patch to provide a passive patch.

Reference to a woven retention device is meant to include an implantable woven, braided, or knitted patch or implantable retention device such as a sleeve. The woven retention device is not intended to be removable. Various embodiments described are meant to be interchangeably used with each other. Furthermore, the terms "aperture" and "pore" are used interchangeably. The terms "filament" and "fiber" are used interchangeably.

Figure 1B:
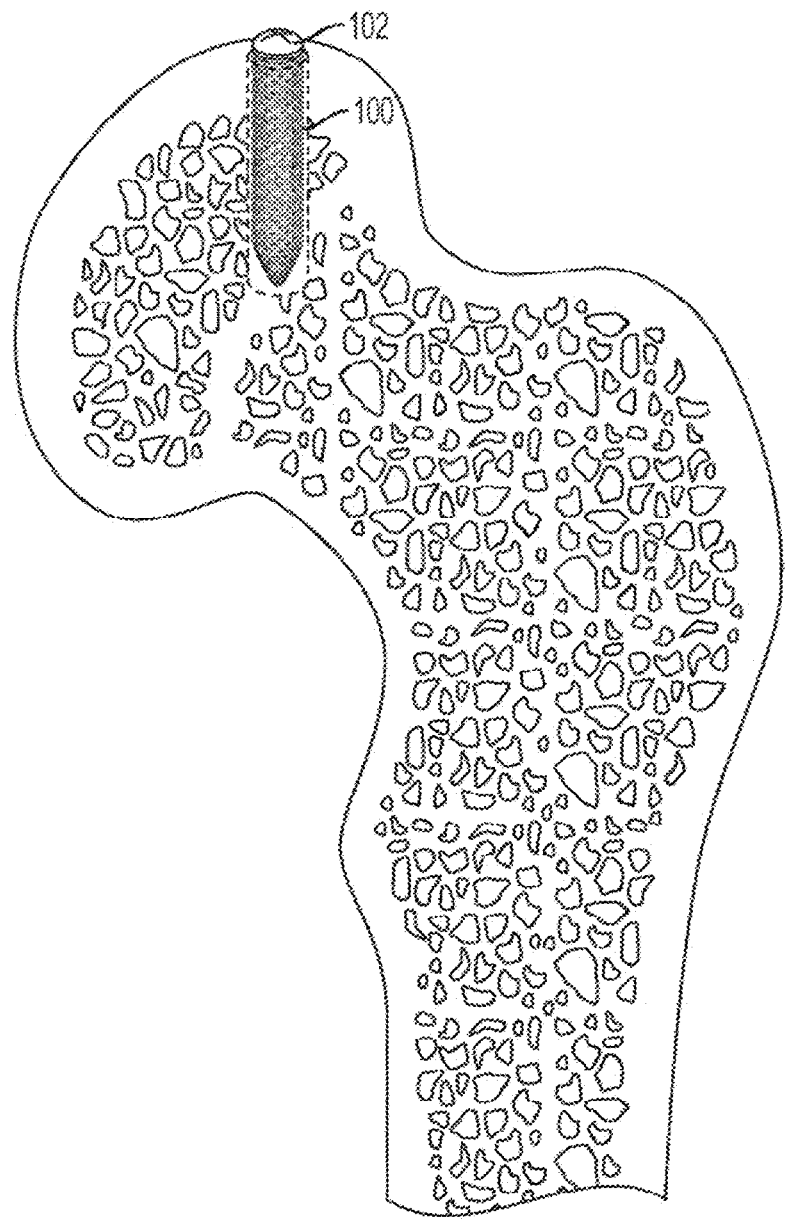
FIG. 1B shows a screw and an implantable retention device fixed inside a bone hole, according to an embodiment of the present invention.

Referring now to the figures, FIGS. 1A and 1B show a woven retention device 100 for interfacing with a bone surface 104, according to an example of an embodiment. The retention device 100, as shown, may have a general configuration or construction in the form of a hollow tubular shape shown as a sleeve body 106 including a plurality of interwoven filaments that may form a substantially tubular lattice. The general configuration of the hollow tubular shape can be selected to accommodate a typical shape of a pilot hole in bone, for example. Various configurations of the sleeve body 106 can be contemplated in accordance with the principles of the invention. The woven retention device 100 can be any of the woven retention devices of co-pending application Ser. Nos. 15/359,021, 15/374,773 and 14/569,542, herein incorporated by reference.

The lattice may include a plurality of protuberances distributed on an interior surface 110 and an exterior surface 108 of the lattice at a predetermined spatial relationship. Each of the plurality of protuberances may be formed by an intersection of filaments. More particularly, each of the plurality of protuberances may be formed by an intersection point of two or more of the plurality of interwoven filaments. The intersection can be referred to as a location and/or point. Additionally, the interwoven filaments may outline apertures that allow for bone ingrowth. The woven retention device can also have a proximal end 114 that is proximal to the sleeve body 106 and that is configured to receive at least a portion of a fastener 102 such that the sleeve body 106 may surround at least a portion of the fastener 102 when inserted therein. The woven retention device 100 can also have a distal end 116 that is distal to the sleeve body 106. In some embodiments, the distal end 116 is formed to ease insertion of the woven retention device 100 into the bone hole 101. For example, the distal end 116 in FIG. 1A is tapered or fused closed. The lattice can be a tubular lattice.

Embodiments of the woven retention device include a woven retention device to promote bone ingrowth or impede biofilm formation. The woven retention device 100 can include a sleeve body 106 comprising a plurality of interwoven filaments that form a substantially tubular lattice with a plurality of protuberances distributed on an interior surface and an exterior surface of the tubular lattice at a predetermined spatial relationship. The woven retention device 100 can include a proximal end that is proximal to the sleeve body and that is configured to receive a fastener; and a distal end that is distal to the sleeve body on an opposing side as the proximal end.

Figure 3:
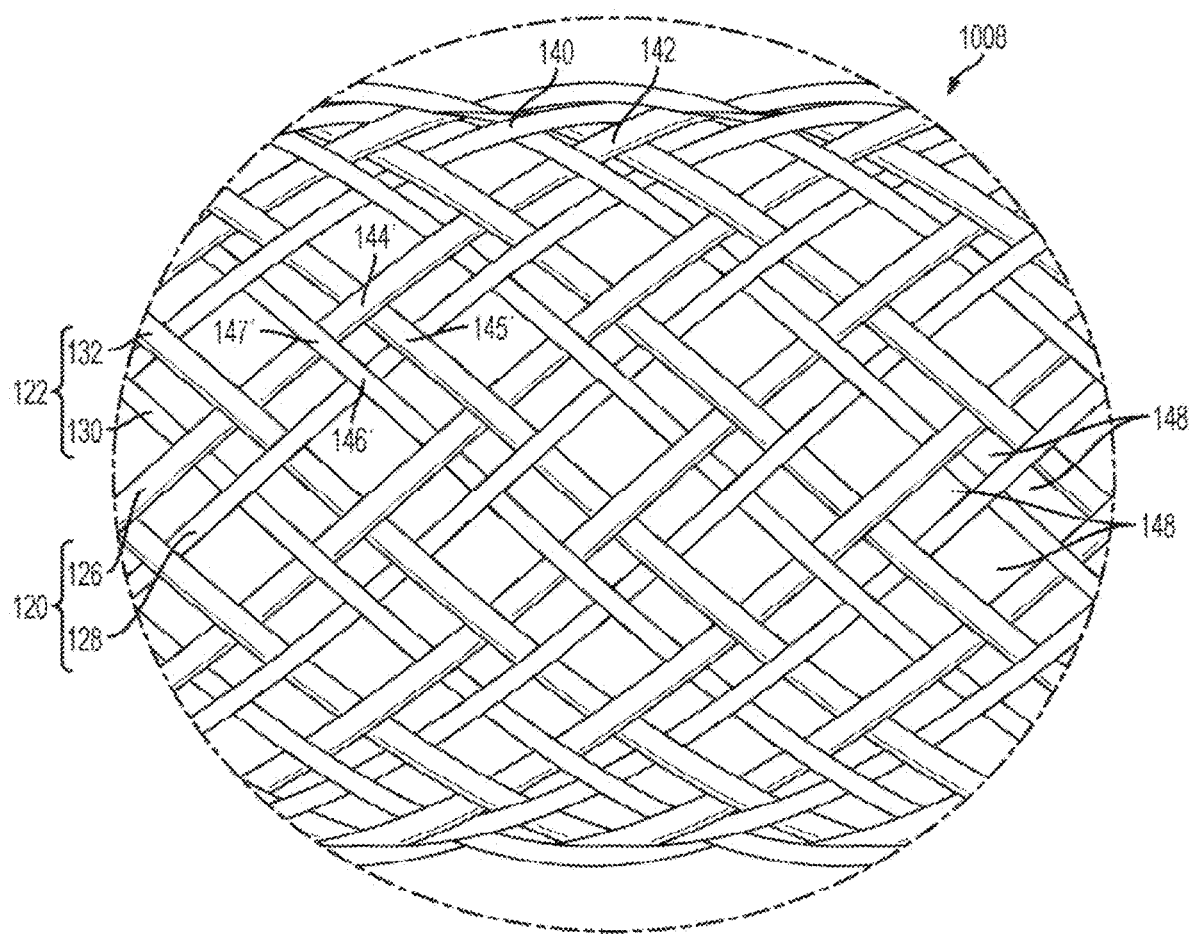
FIG. 3 shows a close-up view of a portion of the implantable retention device shown in FIG. 2.

As can be seen in FIG. 3 and as will be described in greater detail, the woven retention device 1008 can be configured such that the intersecting sets of filaments 120, 122 form a plurality of differently shaped and differently sized apertures or pores 148. In one embodiment, as shown in FIG. 3, the first inner 130 and outer filaments 132 of one set of first filaments 122 can be grouped closer to each other than the other sets 122 of first filaments. Likewise, the second inner 126 and outer filaments 128 of one set 120 of second filaments can be grouped closer to each other than the other sets of second filaments. When the two sets of filaments intersect, as shown in FIG. 3, the area which is outlined by the first and second plurality of sets of filaments is a plurality of differently shaped and differently sized apertures 148.

The area of the apertures can change dynamically by the interwoven filaments translating with respect to each other without substantial stretching or bending of the interwoven filaments. When the woven retention device is in a constricted or expanded state, the aperture areas can change by a function of the braid of the filaments.

The area of the aperture can be in a number of various shapes. For example, as shown in FIG. 3, the apertures 148 can be in a substantially rectangular or square shape. However, other shapes such as circles and ovals are contemplated. The rectangles or square can be of varying sizes. The size of the shape of the aperture can be measured by a height and/or width for a square, triangle or diamond shape, a long and/or short axis for a rectangle, a diameter for a circle, and a major and/or minor axis for an oval. In a relaxed state of the woven retention device, the interwoven filaments can outline apertures having an area along the plane of the tubular lattice. Each area can be defined by a distance between filaments within a range of 200-1000 μm long axis or major axis in the relaxed state.

In a constricted state of the woven retention device 1008, the area of the apertures change as a function of sheath diameter, but each area of the apertures can still fall within the range of 200-1000 μm to promote optimal bone growth. For example, an aperture 148 can be a rectangle having a height of 800 μm in the relaxed state and in a constricted state the aperture can be a rectangle having a height of 500 μm. By having differently shaped and sized apertures, a more conducive environment for contact with non-uniform bony surfaces can allow for ingrowth of bone to occur. Additionally, improved interdigitation with the bony structure can be achieved with a combination of the apertures and protuberances.

For example, at a first diameter, the size of the apertures or pores may be within a predetermined range (e.g. 200-1000 μm) and at a second diameter, the size of the apertures or pores may remain within the predetermined range (e.g. 200-1000 μm). Additionally, in the first diameter, the size of the apertures or pores may be substantially the same as in the second diameter. For example, in the first diameter, the pore size may be about 300 μm and in the second diameter, the pore size may be about 300 μm. For example, in the first diameter, the pore size may be about 300 μm and in the second diameter, the pore size may be any size within the predetermined range (e.g. 200-1000 μm), or vice versa. The first diameter may be a diameter of a woven retention device in a relaxed state and the second diameter may be the diameter of the woven retention device in a constricted state. The first diameter may be a diameter of a first woven retention device and the second diameter may be a diameter of a second woven retention device, where the first woven retention device and the second woven retention device are in the same state (e.g. relaxed or constricted).

The spatial relationship of the protuberances of the woven retention device can affect the formation of biofilms on the fastener and/or on woven retention device. For example, micro-organisms may attach to the fastener and/or the woven retention device. After attachment, the micro-organisms can mature and clog the apertures of the woven retention device. For example, the apertures of the woven retention device allow for porosity that enable bone ingrowth to occur, which facilitates healing. In embodiments of this invention, porosity and pore sizes of the woven retention device are associated with these and other biological responses. For example, very small pore sizes or apertures make the formation of biofilms easier. One of the first stages of development can include 1) initial attachment of the microorganisms, and 2) irreversible attachment (which can lead to buildup). Embodiments of the invention here relate to both phases of preventing initial attachment by the filaments being thin enough and of a material to resist attachment and also having the pore sizes be large enough to prevent irreversible attachment. Thus, larger pore sizes can prevent biofilm attachment. Further, pore sizes can be affected by the degree of the weave intersections. At a 45 degree braid angle, an optimal pore size relationship can be achieved. Thus, even if a biofilm attaches to the filaments, by having large pore sizes, spreading or maturing of the biofilm can be prevented or slowed. Also, other biological responses besides biofilm formation, such as fibrosis, can be prevented with bone ingrowth which relates to the pore size of the woven retention device.

Further there may be some materials that prevent the cellular response of biofilms from building up and maturing. In some embodiments, the woven retention device 100 can include an orthopedic biomaterial that impedes or prevents biofilm attachment or maturation and/or that stimulates or promotes bone growth. Biomaterials in orthopedics can be made of biocompatible, biofunctional, non-toxic, machinable, moldable, extrudable, having tensile strength, yield strength, elastic modulus, corrosion and fatigue resistance, surface finish, creep, hardness. For example, the interwoven filaments can include biomaterials and the biomaterials can be manufactured in fiber format. The woven or non-woven structures described above can be made of non-resorbable or bioabsorbable polymers, metals, biological products or ceramics. Bio resorbable polymer material can be used. For example, the sleeve material can be bioabsorbable and dissolve for complete healing, reduced risk of particulate debris, and have no removal complications as a result. The bioabsorbable polymer can include at least one of thermoplastic aliphatic polyester (PLA), polyglycolide (PGA), polylactide (PLLA) and resorbable polyamides. Alternatively, the sleeve material does not degrade but stays as a structural support of the bone. A non-resorbable polymer material can be biologically suited for use in bone, such as PET (polyethylene terephthalate), ultra high molecular weight polyethylene, polyether etherketone (PEEK), polyether ketoneketone (PEKK), polypropylene, polyamides, PTFE, calcium phosphate and variations of sutures. Additionally, the non-resorbable polymer material may be coated with biologically active osteoinductive materials, such as hydroxyapatite (HA), bone morphogenic protein (BMP), demineralized bone matrix (DBM), and the like.

A hydrophilic biomaterial such as a metal can be hydrophilic and attract bone. In one embodiment, metals can also be used such as titanium, tantalum, nickel titanium (nitinol), platinum, cobalt chrome/cobalt chromium, or a blend of all the listed metals. For example, the metals can include at least one of nickel-titanium (Ni—Ti) or nitinol, stainless steel, platinum, titanium, cobalt chrome, cobalt chromium, or any combination thereof. In an embodiment, the metal material can be roughened to create a roughness characteristic that attracts bone, or encourage bone to grow to it or group to it. In an embodiment, the biomaterial such as a metal can have a radioactive property such that the biomaterial can be detected using electromagnetic radiation, such as X-rays. In one embodiment, the woven retention device can be made of fibers of a bone-promoting biomaterial in combination with fibers of a material that does not promote bone growth. For example, the woven retention device can be made of fibers of titanium, which promotes bone growth, as well as PEEK, which promotes bone growth less. Additionally, fibers of PEKK, which can promote bone growth, can be used in combination with titanium and PEEK. In one embodiment, the filaments can include porous fibers.

In an embodiment, the woven retention device can be constructed with an interior surface having a tap of the metallic biomaterial that follows the path of a fastener such as a screw. In such a configuration, the woven retention device is self-tapped to receive an insert, and as the screw follows the path, the woven retention device is configured to expand. In one embodiment, the self-tapping can be produced through the weaving pattern of the fibers or through a mechanical inscribing process that machines thread that matches to the material into which the woven retention device is being inserted. For example, one metal fiber can be included among all other plastic fibers and based on the pitch of the screw, the metal fiber can be designed to follow the tap of the screw.

Biological materials or biologics, such as silk, collagen, and cat gut suture can be used. See Park and Lakes, "Biomaterials: An Introduction," 1992, Chapter 4 (Park), the content of which is hereby incorporated by reference herein in its entirety. The biological products can include at least one of silk and collagen. Thus, the sleeve can be made of sheet fabric materials such as Silk or Felt that is not woven, but could be created by using collagen. An interior surface could be configured to interface with different structures besides a screw (clamp, smooth, roughened) to provide a strong connection as long as there are many points of contact to provide sufficient sheer strength and a monolithic structure (that is, if one point fails, whole structure does not fail).

The woven retention device 100 can be inserted into a hole in a bone and interact with both the bone and a screw. While the woven retention device 100 can achieve an interference fit functionality by providing additional interference in between the fastener and the bone, in some embodiments, the woven retention device can instead of and/or in addition to function as a woven retention device in accordance with the configurations, functions and advantages that are discussed herein. For example, the woven retention device can have a dual interface between a radial screw surface on one side and multiple points of contact on a bone surface on the other side. The dual interfaces on the retention device are configured to be adapted to the bony structure on the outside and the screw on the inside, as described herein in accordance with the principles of the invention. The woven retention device can be particularly beneficial for osteoporotic or weakened bone that has more space gaps than normal bone to allow additional points of contact for the interface to contact.

FIG. 1A shows the woven retention device 100 in an exploded state with the fastener 102 outside of the retention device, and both the fastener 102 and the retention device 100 are outside of the bone hole. FIG. 1B shows the fastener 102 inside the woven retention device 100, which is inside the bone. FIGS. 1A and 1B also illustrate an example of a porous interior structure of the bone. However, embodiments of the invention are not limited to being used with the exact porous structure shown, as the structure and porosity of bone can vary. In addition, although the bone illustrated in FIGS. 1A and 1B resembles a human femur, embodiments of the invention are not limited to a particular bone. An advantage of some embodiments of the invention is that a woven retention device can be provided for use in a variety of bones and bones exhibiting varying levels of porosity.

Thus, a woven retention device 100 for interfacing with a bone surface can include a sleeve body 106 comprising a plurality of filaments forming a substantially tubular lattice with a plurality of protuberances distributed on an interior surface and an exterior surface of the tubular lattice at a predetermined spatial relationship. The sleeve body 106 can be configured to surround at least a portion of a fastener 102. Each of the plurality of protuberances can be formed by an intersection point of two or more of the plurality of filaments that outline a plurality of apertures. The sleeve body 106 can include an orthopedic biomaterial The woven retention device 100 can include a proximal end 114 that is proximal to the sleeve body and that is configured to receive at least a portion of the fastener 102. The woven retention device 100 can include a distal end 116 that is distal to the sleeve body. In a first state, the sleeve body 106 has a plurality of combinations of filament cross-section geometries at the intersection points, the plurality of combinations of filament cross-section geometries forming a plurality of protuberance thicknesses, a thickness of each protuberance being measured in a radial direction of the sleeve body. In a second state when a fastener is inserted into the tubular lattice, pressure from the fastener 102 can be transmitted to the tubular lattice such that the spatial relationship of the protuberances changes according to a function of bone density and according to a function of an interfacing surface shape of the fastener.

The woven retention device 100 can thus be configured to impede biofilm formation. The biomaterial of the woven retention device 100 can be made of a material that impedes biofilm formation. The sleeve body can have a structure that impedes biofilm formation.

The retention device 100 can thus be configured to promote bone ingrowth. The biomaterial of the woven retention device 100 can be made of a material that promotes bone formation. The sleeve body can have a structure that promotes bone ingrowth.

The sleeve body can be configured to receive a portion of the soft tissue and the sleeve body is configured to impede biofilm formation surrounding the soft tissue. The sleeve body comprises a coating on the plurality of filaments, wherein the coating comprises an orthopedic biomaterial. The plurality of filaments can comprise the orthopedic biomaterial.

Figure 1C:
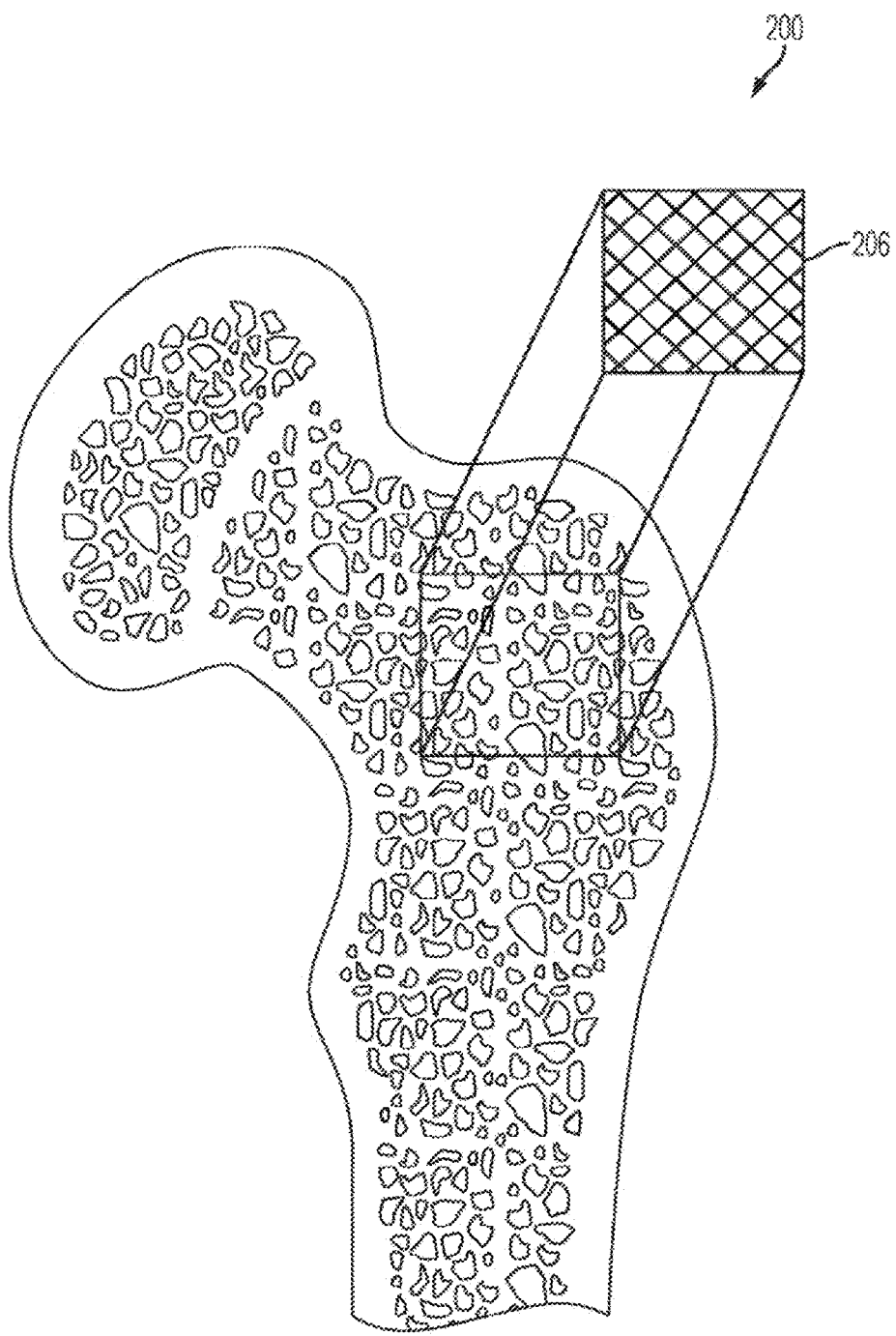
FIG. 1C shows a perspective view of a screw, a woven patch and a bone, according to an embodiment of the present invention.

Referring now to the figures, FIG. 1C shows a woven sleeve or patch 200 in an exploded state outside of the bone placement for interfacing with a bone surface, according to an example of an embodiment. The patch 200, as shown, may have a general configuration or construction in the form of a patch shown as a sleeve body 206 including a plurality of interwoven filaments that may form a lattice. The general configuration of the lattice can be flat and adapted to accommodate a typical shape of a bone, for example. The woven patch can have a degree of elasticity (ability to return to the woven patch to return to the original/nature shape) or flexibility to adapt to various bone structures. The woven patch can be elastically formed into various sizes by the translation of the woven or braided fibers that does change the interstices sizes while adapting to various bone structures. Additionally, various configurations of the sleeve body 206 can be contemplated in accordance with the principles of the invention.

The lattice may include a plurality of protuberances distributed on a first surface, or an interior surface, and a second surface, or an exterior surface, of the lattice at a predetermined spatial relationship. Each of the plurality of protuberances may be formed by an intersection of filaments. More particularly, each of the plurality of protuberances may be formed by an intersection point of two or more of the plurality of interwoven filaments. The intersection can be referred to as a location and/or point. Additionally, the interwoven filaments may outline interstices that allow for bone ingrowth. The woven patch can also have a proximal end that is proximal to the sleeve body 206 and that is configured to be applied to at least a portion of a fastener (not depicted). The woven patch 200 can also have a distal end that is distal to the sleeve body 206. In some embodiments, the distal end is formed to ease insertion of the woven patch 200. For example, the distal end in FIG. 1C is tapered or closed. The lattice can be a tubular lattice.

The woven patch 200 can be applied to a bone and interact with both the bone and a screw. While the woven patch 200 can achieve an interference fit functionality by providing additional interference in between a fastener and the bone, in some embodiments, the woven patch can instead of and/or in addition to function as a woven patch in accordance with the configurations, functions and advantages that are discussed herein. For example, the woven patch can have a dual interface between a radial screw surface on one side and multiple points of contact on a bone surface on the other side. The dual interfaces on the patch are configured to be adapted to the bony structure on the outside and the screw on the inside, as described herein in accordance with the principles of the invention. The woven patch can be particularly beneficial for osteoporotic or weakened bone that has more space gaps than normal bone to allow additional points of contact for the interface to contact. The woven patch 200 may any of those described in co-pending application Ser. Nos. 15/359,021, 15/374,773 and 14/569,542, herein incorporated by reference. It may be appreciated that the functions and properties of the woven retention device 100 describe herein may also apply to the woven patch 200.

As discussed in detail further below, the plurality of interwoven filaments may include one or more varieties of filament shapes and sizes such that the sleeve body 106 can have a plurality of combinations of filament cross-section geometries at the intersection of the filaments, which can also be referred to as intersection points of the filaments. Because each intersection of the filaments may form a protuberance, the plurality of combinations of filament cross-section geometries may form a plurality of protuberance thicknesses, each thickness being measured in a radial direction of the sleeve body 106. For example, a cross-section geometry can include a shape of the cross-section and/or a size of the cross-section. The combination of the filament cross-section geometries can include the cross-section geometries of both filaments at the intersection. The combination of filament cross-section geometries can form a plurality of interstices sizes and shapes to promote bone ingrowth.

The spatial relationship of the plurality of protuberances and the plurality of interstices can also change as a function of loading and/or the fastener. The spatial relationship of the plurality of protuberances and apertures can change as a function of an interfacing surface shape of the fastener 102. In one embodiment, where the screw has a larger pitch, for instance in a larger size of screw, the retention device when interfacing with the screw can change to accommodate the coarse threads. For example, the retention device can adapt to follow the crests and the valleys to create a general wave pattern. On the other hand, in the case of a smaller diameter screw, or a finer thread with smaller pitch, the retention device can deform or bend over the peaks of the threads less. Thus, in one embodiment, the absolute value of pullout resistance can be greater with a larger screw but the delta between the differential can be smaller with the larger diameter screw because of additional interwinding of the intermediary point of contact. That is, in one embodiment, the protuberances on the exterior surface do not interface as much with the bone because of some of the protuberances folding inward because of the coarseness of the thread. Whereas on the small diameter screw, the woven retention device can move more uniformly, which can allow for greater interdigitation. Thus, because there can be less chance for those interdigitation points to reach into the valleys of the threads, there is more interaction with the bony surface. The greater interaction on the bony surface also enhances and increases the amount of contact of the interstices to the bone surface to promote bone ingrowth.

The spatial relationship of the plurality of protuberances and the plurality of interstices can also change as a function of an interfacing surface shape based on the length of the surface. For example, the surface of the fastener 102 can also be various lengths. Even though the change in pullout resistance can be greater with large screws than small screws in total pullout resistance, the small screw can have greater pullout resistance as a measure of percent change. One factor that affects the small screw having a greater pullout resistance in percent change is that more interaction with the woven retention device 100 can be possible with a smaller fastener as a percentage of the fastener's percentage of coverage. This can result in a larger differential in pull out resistance in the smaller sizes than there is in the larger sizes because of the increased interaction. In one embodiment, the mechanical properties of the woven retention device can compensate for differences in the fastener surface. For example, to increase bone surface interaction with a fastener 102 that has a coarse thread, a woven retention device with a greater level of stability can be used to prevent the filaments from retreating too far into the valleys and instead interacting with the bone surface.

In some embodiments, the woven retention device 100 may be specifically configured for a bone of a particular density or range of densities. For example, the structural configuration, material properties, or other aspects of the woven retention device may be adjusted to provide desired engagement with the bone surface of a particular density or range of densities. However, in some embodiments, a particular woven retention device may be suitable for use in bones of varying densities.

FIG. 2 shows the woven retention device 1008 with a tapered distal end 116 along its longitudinal axis. The tapered distal end 116 may taper to a distal tip 115 that has a smaller diameter than the sleeve body 106. The woven retention device 1008 may be the same or similar to the woven retention device 100.

FIG. 3 shows a close-up view of the woven retention device 1008 of FIG. 2, according to one embodiment. As explained below, a set of filaments can include one or more filaments. In one embodiment, a set of filaments can include filaments that are side by side and the filaments including an inner filament and an outer filament. The inner filament in one embodiment can be disposed on the left of the outer filament, as viewed facing the receiving portion in a longitudinal direction. For example, FIG. 3 shows one embodiment of a woven retention device 1008, wherein each of the first plurality of sets of filaments 120 includes a first inner filament 126 and a first outer filament 128, and each of the second plurality of sets of filaments 122 includes a second inner filament 132 and a second outer filament 130. In one embodiment, one of the outer filaments and the inner filaments can be a round monofilament 140 and one of the outer filaments and the inner filaments can be a flat multifilament 142. However, in another embodiment, filament 142 can be a round monofilament with a different or a same diameter as monofilament 140. In one embodiment, the woven retention device 1008 is configured such that the plurality of interwoven filaments are comprised of alternating round monofilaments and flat multifilaments. In this embodiment, each of the sets of filaments can have a consistent and uniform order of filaments, which allows for a uniform arrangement of protuberances. In another embodiment, the plurality of interwoven filaments are comprised of alternating round monofilaments of a first diameter and round filaments of a second diameter that is greater than or less than the first diameter.

As shown in FIG. 3, in one embodiment, the first inner filament 126 can be a flat multifilament 142, the first outer filament 128 can be a round monofilament 140, the second inner filament 132 can be a flat multifilament 142 and the second outer filament 130 can be a round monofilament 140. However, it may be appreciated that different monofilament/multifilament arrangements may be employed.

Each of the different monofilament/multifilament arrangements allow for the protuberances to occur at different regions. In FIG. 3, the protuberances form a diamond arrangement shown by the shape defined by intersection points 144', 145', 146', and 147'.

Each of the different monofilament/multifilament arrangements allow for interstices to occur at different regions. In FIG. 3 the interstices form a diamond arrangement by the shape defined by the space captured by intersection points 144', 145', 146', and 147'.

As can be seen from FIG. 3, the woven retention device 1008 can be configured so that the plurality of interwoven filaments follow a two-under/two-over configuration, where each of the filaments overlie two intersecting filaments and underlie two intersecting filaments. In another embodiment, at each intersection point, a round monofilament either overlies both of the intersecting filaments or is overlain by both of the intersecting filaments and the flat multifilament overlies one of the intersecting filaments and is overlain by the other of the intersecting filaments. However, other contemplated embodiments include a one-over-one weave provided that there is sufficient rigidity and flexibility of the filaments to generate the protuberances.

For FIG. 3, alternative weaving patterns besides the two-over/two-under configuration are also contemplated within the broad inventive principles disclosed herein. A one-over/one-under configuration is contemplated where each filament alternatingly overlies and underlies an intersecting filament. In one embodiment, a three-over/three-under weave pattern is contemplated where each filament overlies three intersecting filaments before underlying three intersecting filaments. In another embodiment, a two-over/one-under is contemplated where each filament overlies two intersecting filaments and then underlies one intersecting filament. Alternatively, a one-over/two-under arrangement is also possible where a filament overlies one intersecting filament before underlying two intersecting filaments. In another embodiment, a three-over/one-under is contemplated where each filament overlies three intersecting filaments and then underlies one intersecting filament. Alternatively, a one-over/three-under arrangement is also possible where a filament overlies one intersecting filament before underlying three intersecting filaments. With each of these weaving patterns, sufficient stability, rigidity, compressibility, sheer strength, and/or tensile strength can allow for the pressure from the fastener is able to transmit force in a distributed manner to the bone surface.

The round monofilaments of the woven retention device can have differing diameters. In one embodiment, the round monofilaments can have a diameter in a range of about 0.1 mm-0.4 mm. In one embodiment, the round monofilament of the woven retention device is 0.2 mm. In another embodiment, the round monofilaments can have alternating monofilaments of different diameters.

The multifilaments of the woven retention device according to some embodiments can have various thicknesses and widths. For example, a multifilament may have a thickness of less than 0.1 mm. The cross-sectional shape, e.g., flat or round, and the texture, for example, of the multifilaments can also be relevant. The number of filaments and pattern can also be relevant. As such, with those considerations, various filament linear mass densities can be contemplated. For example, the multifilaments can have a linear mass density in a range of about 150-250 denier. In one embodiment, the multifilaments can have a linear mass density of about 200 denier.

The woven retention device can be configured such that the intersecting sets of filaments form a plurality of differently shaped and differently sized apertures or pores. In one embodiment, as shown in FIG. 3, the first inner and outer filaments of one set of first filaments can be grouped closer to each other than the other sets of first filaments. Likewise, the second inner and outer filaments of one set of second filaments can be grouped closer to each other than the other sets of second filaments. When the two sets of filaments intersect, as shown in FIG. 3, the area which is outlined by the first and second plurality of sets of filaments is a plurality of differently shaped and differently sized apertures 148. By having differently shaped and sized apertures, a more conducive environment for non-uniform bony surface can allow for ingrowth of bone to occur. Additionally, improved interdigitation with the bony structure can be achieved with a combination of the apertures and protuberances.

Figure 11:
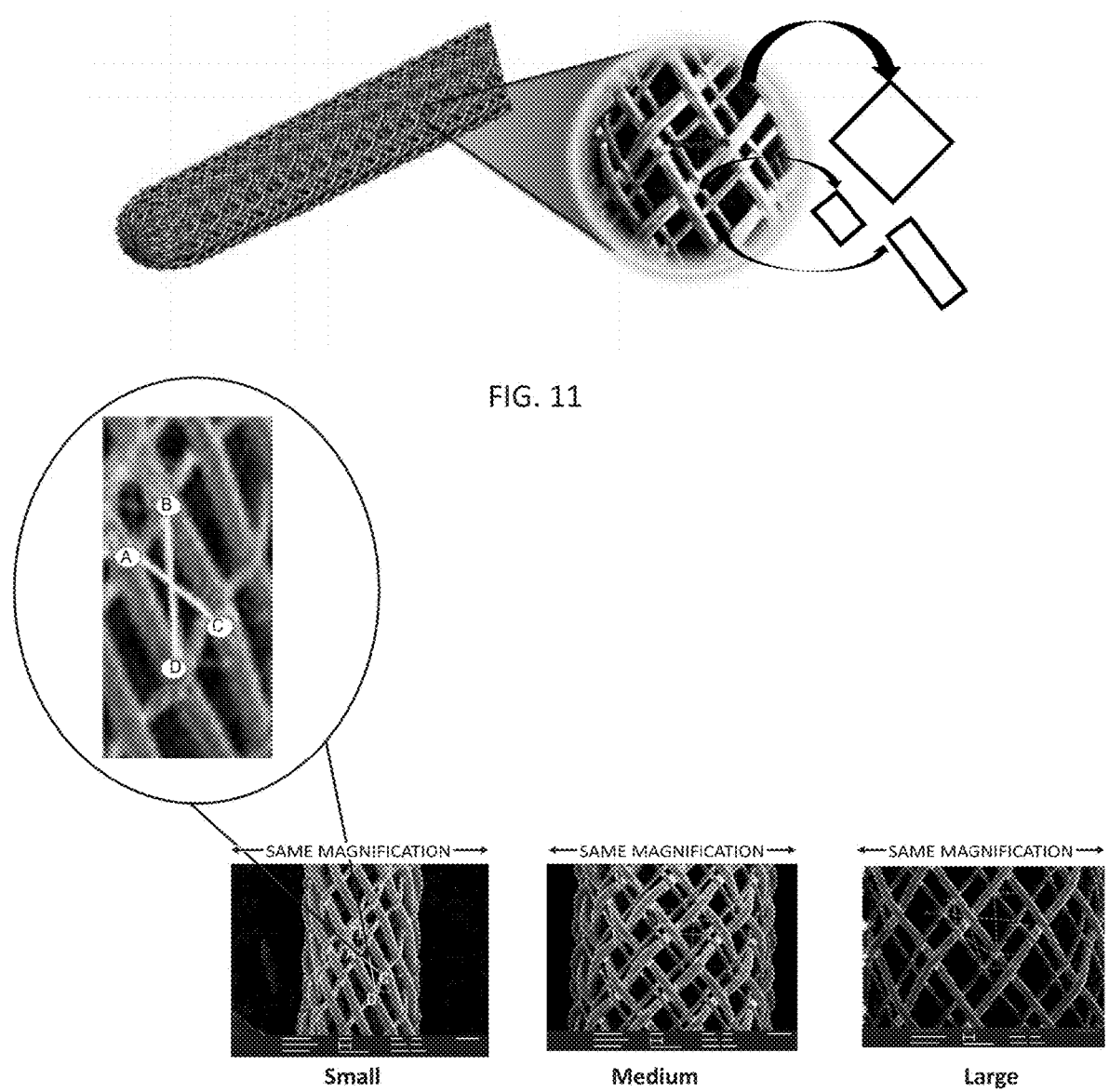
FIG. 11 shows an exemplary pore shape of a woven retention device, according to embodiments of the present invention.

In one embodiment, the intersecting sets of filaments create parallelograms of open space or pores 148 (see FIG. 11). The pores 148 have a pore size defined by a diagonal corner to corner length. That is, the pore size is defined by the 3-dimensional distance between fiber surfaces. For example, for the parallelogram pores shown in FIG. 11, the pore size can be described as the length between opposing diagonal corners. In an exemplary embodiment, the pore size may be in a predetermined range of 200-1000 µm. That is, the minimum pore size is 200 µm (e.g. a minimum 3-dimensional linear distance between fibers) and the maximum pore size is 1000 µm (e.g. a maximum 3-dimensional linear distance between fibers).

In an exemplary embodiment, the average pore size is about 600 µm. In an exemplary embodiment, the average pore size is about 600 µm+/−200 µm. In an exemplary embodiment, the average pore size is about 600 µm+/−400 µm. In an exemplary embodiment, the minimum pore size is about 400 µm and the maximum pore size is about 800 µm. In an exemplary embodiment, the minimum pore size is about 400 µm and the maximum pore size is about 600 µm. In an exemplary embodiment, the minimum pore size is about 600 µm and the maximum pore size is about 800 µm. In an exemplary embodiment, the minimum pore size is about 200 µm and the maximum pore size is about 1000 µm. In an exemplary embodiment, the minimum pore size is about 200 µm and the maximum pore size is about 600 µm. In an exemplary embodiment, the minimum pore size is about 600 µm and the maximum pore size is about 1000 µm. In exemplary embodiment, the minimum pore size is about 100 µm and the maximum pore size is about 1100 µm. Although the pore size has been described in relation to the 3-dimensional distance between fibers, it may be appreciated that pore size may be measured in other manners. For example, the pores may be defined as a volume of space between the fibers. The pore size may thus be defined as the distance from the geometric center of the volume of space to any fiber.

As may be appreciated, since the pore size is defined by the fiber spacing, the pore size may also be defined by the braiding parameters, as will be discussed in more detail below. That is, the under/over arrangement and location of the different fiber sizes (e.g. alternating spools of 0.2 mm and 0.3 mm fiber on the bobbins located on the circumference of the spindle) on the bobbins, the picks per inch, and the braid angle. The natural compression and expansion diameter range of the woven retention device may be defined by the braiding parameters, as described in Tables 1-3.

The following parameters define the large (6.5 mm) size:

TABLE 1

Exemplary braiding parameters for large woven retention device.

| Counter Clockwise Bobbins | | | | Clockwise Bobbins | | | |
|---|---|---|---|---|---|---|---|
| Size (mm) | # of Carriers | Size (mm) | # of Carriers | Size (mm) | # of carriers | Size (mm) | # of Carriers |
| 0.2 | 12 | 0.3 | 12 | 0.2 | 12 | 0.3 | 12 |

Pattern: 3 0.3 mm fibers for every 1 0.2 mm fibers, producing a 2-over, 2-under pattern
Braid angle: 40-45 degrees
Pick count: 25 picks per inch In exemplary embodiments, the braid angle may be 35-50 degrees. In exemplary embodiments, the pick count may be 20-35 picks per inch.

The following parameters define the small (2.0 mm) size:

TABLE 2

Exemplary braiding parameters for small woven retention device.

| Counter Clockwise Bobbins | | | | Clockwise Bobbins | | | |
|---|---|---|---|---|---|---|---|
| Size (mm) | # of Carriers | Size (mm) | # of Carriers | Size (mm) | # of carriers | Size (mm) | # of Carriers |
| 0.2 | 12 | 0.3 | 12 | 0.2 | 12 | 0.3 | 12 |

Pattern: 1 0.2 mm fiber for every 1 0.1 mm fiber, producing a 2-over,2-under pattern
Braid angle: 40-45 degrees
Pick count: 45 picks per inch In exemplary embodiments, the braid angle may be 35-50 degrees. In exemplary embodiments, the pick count may be 35-35 picks per inch.

The following parameters define the medium (3.5 mm) size:

TABLE 3

Exemplary braiding parameters for medium woven retention device.

| Counter Clockwise Bobbins | | | | Clockwise Bobbins | | | |
|---|---|---|---|---|---|---|---|
| Size (mm) | # of Carriers | Size (mm) | # of Carriers | Size (mm) | # of carriers | Size (mm) | # of Carriers |
| 0.1 | 12 | 0.2 | 12 | 0.1 | 12 | 0.2 | 12 |

Pattern: 1 0.2 mm fiber for every 1 0.1 mm fiber, producing a 2-over,2-under pattern
Braid angle: 40-45 degrees
Pick count: 47 picks per inch In exemplary embodiments, the braid angle may be 35-50 degrees. In exemplary embodiments, the pick count may be 37-57 picks per inch.

It has been demonstrated that bone desires a certain pore size to promote growth. The woven retention device may be compressed into a bone hole and then expanded by a screw (such as fastener 102) as the screw is inserted into the woven retention device. The pores 148 of the woven retention device stay within a pore size range that is optimal for bone growth. The pores 148 remain in the pore size range regardless if the diameter of the woven retention device is compressed or expanded to ensure bone growth can occur regardless of the bone hole size in which it is inserted. As discussed above, the pore size predetermined range may be 200-1000 μm. The compression or expansion of the woven retention device is accomplished by the translation of the fibers with respect to each other, which in turn decreases or increase the pore size. Thus, the pore size may be different for different woven retention device diameters but within the optimal range for bone ingrowth.

In embodiments, the woven retention device size, e.g. the diameter of the woven retention device is determined for a bone hole size where a certain amount of fiber translation and uniform diameter change may occur without altering the circular cross-sectional shape of the woven retention device and provide the optimal engagement of the protuberances with the bone.

It may be appreciated that the woven retention device for each size (e.g. small, medium, large, XL) was selected so the pore size range remained the same for each woven retention device size. If the braiding parameters are held constant for each size and the overall diameter of the woven retention device was increased, the pore size would be altered. FIGS. 12a, 12b, and 12c show the same woven retention device scaled up in diameter, all in the relaxed position. The fiber coverage (density) decreases as the pore size increases as the diameter is increased.

A 3-dimensional distance may be the distance between two points in 3-dimensional space, that is, where the two points are not in the same plane. For example, in the case of a parallelepiped, such as is provided in the woven retention devices of FIGS. 12a-12c, the four corners of one face of the parallelepiped may be labeled A, B, C, and D. The 3-dimensional distance may be the distance between points A and C, for example. Due to the curvature of the woven retention devices, these points may not lie in the same plane, and as such, the distance between the points may be thought of as a 3-dimensional distance. The 3-dimensional distance may define the pore size. The pore size may remain within the predetermined range regardless of the diameter of the woven retention device. Thus, it may be appreciated that the pore size is the same in each of FIGS. 12a, 12b, 12c.

The braiding parameters were modified for each woven retention device size to maintain the same fiber volume and pore size. The small, medium, and large woven retention device are formed with the same fiber volume and same pore size by varying the fiber size, number of fibers (e.g. number of bobbins), pick count, and/or braid angle, or any combination thereof. Each woven retention device size is unique with respect to the braiding parameters. Each woven retention device pore geometry may be defined by the braiding parameters. Referring to Table 4, the total number of fibers is 48 for the large woven retention device, 48 for the medium woven retention device, and 24 for the small woven retention device. For example, referring back to Table 1, the large woven retention device may have 12 fibers of 0.2 mm diameter from the counter clockwise bobbins, 12 fibers of 0.3 mm diameter form the counter clockwise bobbins, 12 fibers of 0.2 mm diameter from the clockwise bobbins, and 12 fibers of 0.3 mm diameter from the clockwise bobbins, for a total of 48 fibers. In another exemplary embodiment, the medium woven retention device geometry is further defined by the 2 under/2-over pattern, the location of the different fiber sizes (e.g. alternating spools of 0.2 mm and 0.3 mm fiber on the bobbins located on the circumference of the spindle) on the bobbins, the chosen 29 picks per inch, and the 45° braid angle.

TABLE 4

Exemplary fiber diameters and fiber numbers for different woven retention devices

|  | Small | Medium | Large |
|---|---|---|---|
| Size of Fibers | 0.2 & 0.1 mm | 0.2 & 0.1 mm | 0.3 & 0.2 mm |
| No. of Fibers | 24 | 48 | 48 |

The interwoven filaments of a woven retention device extend around the tubular lattice in an angle range. In one embodiment, the angle can represent a range from about 40-60 degrees with respect to a longitudinal direction of the woven retention device. In another embodiment, the angle can represent a range from about 15-75 degrees with respect to a longitudinal direction of the body sleeve. In one embodiment, the angle represents 45 degrees. The retention device can, in the relaxed state, have the interwoven filaments that extend around the tubular lattice at about a 45 degree angle with respect to a longitudinal direction of the woven retention device.

According to another embodiment, the braid angle can be smaller than 45 degrees. According to another embodiment, when the woven retention device has an average diameter of 2 mm, the braid angle can be about 35 degrees.

An exemplary method of braiding a woven retention device, such as woven retention devices 100 and 1008, will be described. The fibers or filaments may be spooled on bobbins in a circumference and rotated in a "maypole" pattern together to create the cylindrical braid. The fibers/filaments converge on a mandrel to create a cylindrically shaped braid. The bobbins placed along a large circumference. Each bobbin contains a spool of fiber/filaments. The fibers/filaments converge to the center of the large spindle to create the braided cylinder. The braiding process may be the one shown and described in co-pending application Ser. Nos. 14/569,541 and 15/374,773, herein incorporated by reference.

The pore shape is illustrated as a 2-dimensional parallelogram in the side longitudinal view of the woven retention device (FIG. 11). The actual 3 dimensional shape is a parallelepiped that creates a parallelogram-shaped aperture for bone to grow into and through.

The braiding pattern creates a varying 3-dimensional pore size and shape that creates a complex asymmetrical network of pores. The pores vary in size, shape and orientation on the braided sleeve, as illustrated in FIG. 11 Although the pores appear to be 2-dimensional (e.g. parallelograms), the cylindrical braid pattern actually forms 3-dimensional shapes (e.g. parallelepiped apertures) that are orientated in multiple directions. The 3-dimensional shapes or volumes formed by the fibers create "tunnels" (e.g. empty spaces) for bone to growth into in all directions through the sleeve. For example, bone is able to grow radially through a pore towards the center longitudinal axis of the sleeve, around the circumference of the sleeve, or tangentially from the outer circumference of the sleeve through the sleeve thickness and then outward through the thickness at another location on the circumference. The boundaries of the parallelepiped open space/volumes are created by cylindrical monofilament fiber surfaces. The monofilament fibers form the boundaries by crossing under and over each other. Since the fibers/filaments can translate with respect to each other and are not fused together along their lengths, there are small gaps between them along their length. Bone is not blocked from growing into and through these spaces. Therefore, there are always 3 directions for which bone to form, creating a complex 3 dimensional network of bone cells that can connect in all directions at each pore.

Figure 13:
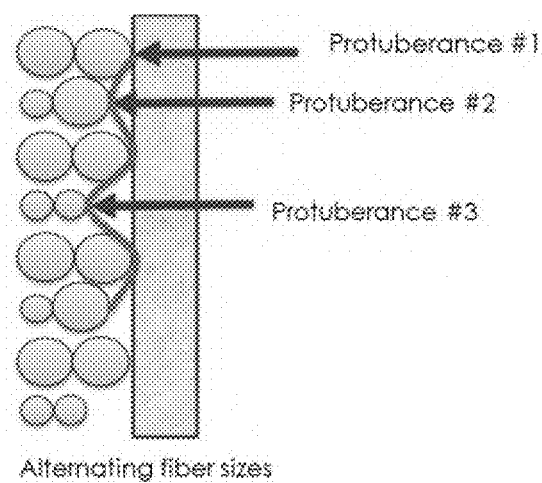
FIG. 13 shows a schematic of a woven retention device, according to an embodiment of the present invention.
Figure 14:
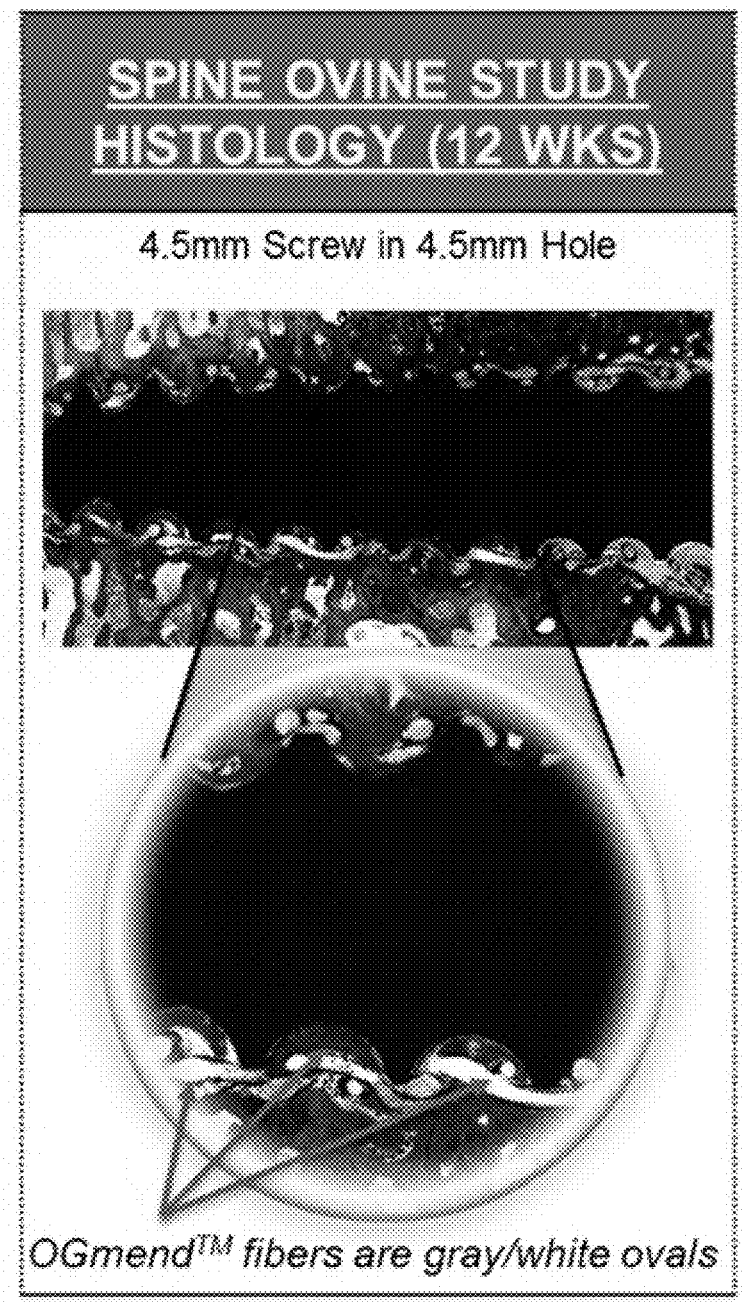
FIG. 14 shows an exemplary bone growth in a study, according to embodiments of the present invention.

The pores create a complex 3-dimensional interface with the bone complementary to the varying protuberance thickness that creates a complex mechanical interface with the bone. The pore interface is not a mechanical transfer of load as the protuberance is, but a space into which bone can respond. That is, the protuberances are created by the fibers and directly touch the bone. The pores also touch the bone when the bone is permitted to grow into the pores. By optimizing the pore size (through optimizing the braid pattern), the woven retention device achieves both the protuberances for transferring of load and the pores to promote optimal bone growth. Alternating protuberances create alternating pores for bone growth. For example, the diagram of FIG. 13 illustrates the varying sized protuberances in 1 direction, and the associated varying sized pores adjacent to them. FIG. 13 is a schematic which represents the cross-section of the device, cut-away into the opening. The protuberances actually vary in 3 dimensions and similarly the pores vary in 3 dimensions as well.

The protuberances vary in thickness and shape, interdigitating with the trabeculae of the bone hole, as disclosed in co-pending application Ser. No. 15/359,021 and 14/569,542, herein incorporated by reference. Similarly, there is intimate contact of the pore with bone, facilitating bone growth from the bone hole through the pore for varying bone densities.

In one embodiment, the woven retention device can have a length in a range of about 30 mm to 150 mm. The length of the woven retention device can come in dynamically cuttable; and/or predetermined length, such as small—30 mm; medium—40 mm, large—40 mm, and other sizes (or ranges) are also possible. In one embodiment, the woven retention device can have a diameter of about 1.5 mm to 10.0 mm. The diameter of the woven retention device can come in predetermined sizes, such as (i) small: 2.0 mm fine (can accommodate 1.3 mm to a little over 2.0 mm pilot hole diameter and can fit 2.0 mm-2.7 mm screws); (ii) medium: 3.5 mm-6.0 mm course (can accommodate 2.4 mm to a little over 3.2 mm pilot hole diameters and can fit 3.5-6 mm screws); and (iii) large: 6.5 mm-9 mm very course (can accommodate 4.1 mm to a little over 5.9 mm pilot hole diameters and can fit 6.5-9.0 mm screws).

In a relaxed state, the woven patch can be of various lengths and diameters. In one embodiment, the woven patch can have a length in a range of about 10 mm to 150 mm. In an embodiment, the woven patch can have a length in a range of about 30 mm to 60 mm. The length of the woven patch can come in dynamically cuttable; and/or predetermined length, such as small—30 mm; medium—40 mm, large—40 mm, and other sizes (or ranges) are also possible.

The sleeve can work at filling the hole better to provide more points of contact for the bone interface. One way it can do so is by having two sleeves nested, which can add additional advantages using the multiple points of contact interface. It can also have a homogeneous and uniform interface for screw engagement so that a number of characteristics of the sleeve can be achieved: Rigidity, Compressibility, Stability, Sheer strength (at a predetermined level), Tensile strength (at a predetermined level). The implantable retention device can be made of at least one of silk, non-woven felt, and collagen.

Figure 4:
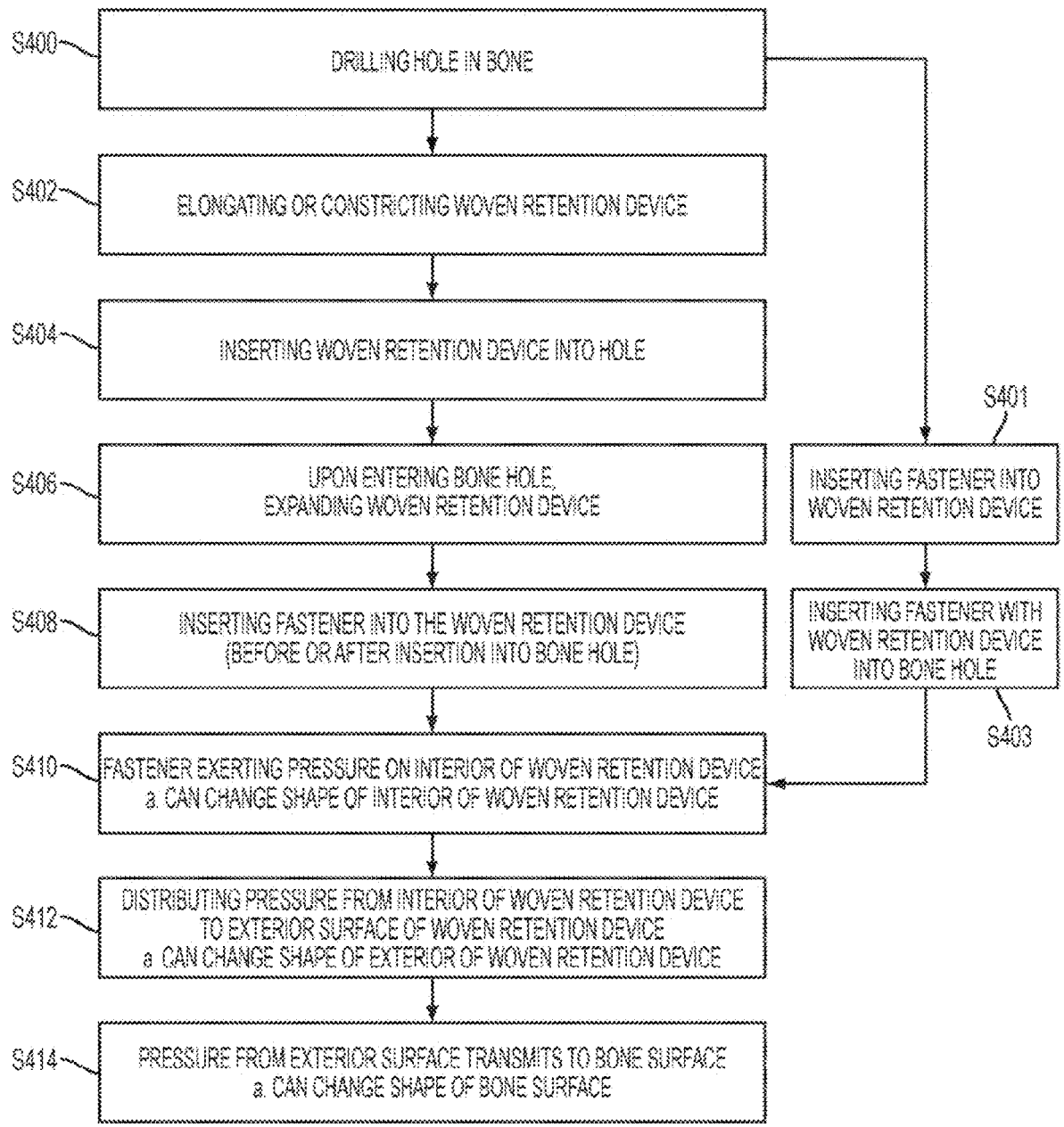
FIG. 4 shows a flow diagram of a method of utilizing an implantable retention device in an embodiment, in accordance with the principles of the present invention.

Various methods of using the woven retention device can be used. FIG. 4 details steps that can be performed in conjunction with the woven retention device. The woven retention device may be inserted into a bone hole alone and then a fastener can be inserted. Alternatively, the woven retention device and screw can we combined prior to insertion and the combination inserted into the bone hole. The invention is not limited to the steps described in FIG. 4, is not limited to the order of the steps disclosed, and does not require that certain of the disclosed steps be performed.

In one embodiment, in step S400, a bone can be drilled to form a bone hole. In one embodiment, the woven retention device can be elongated or constricted in step S402, after which in step S404 the woven retention device can be inserted into the bone hole. After step S404, in step S406 the woven retention device upon entering the bone hole can be expanded. Thus, upon entering the bone hole, the woven retention device can expand to a less elongated and constricted state to interface with the bone surface. After step S406, in step S408 the fastener can be inserted into the woven retention device either before or after insertion into the bone hole. Next, the fastener can exert pressure on an interior of the woven retention device in step S410. In step S410, the fastener can optionally change the shape of the interior of the woven retention device. Next, in step S412, pressure from an interior of the woven retention device can be distributed to an exterior surface of the woven retention device. In step S412, the shape of the exterior surface of the woven retention device can optionally change shape. In step S414, pressure from an exterior surface of the woven retention device can transmit to bone surface. In step S414, the pressure transmission to the bone surface can optionally change the shape of the bone surface. In other embodiments, the steps can be performed in different orders or steps can be optionally omitted.

In another embodiment, instead of following steps S402, S404, S406 and S408, in step S401, a fastener can be inserted into the woven retention device before the woven retention device has been inserted into the bone hole, after which in step S403 the fastener with woven retention device can be inserted into the bone hole. After step S403, in step S410 the fastener can optionally change the shape of the interior of the woven retention device. Next, in step S412, pressure from an interior of the woven retention device can be distributed to an exterior surface of the woven retention device. In step S412, the shape of the exterior surface of the woven retention device can optionally change shape. In step S414, pressure from an exterior surface of the woven retention device can transmit to bone surface. In step S414, the pressure transmission to the bone surface can optionally change the shape of the bone surface.

Figure 5:
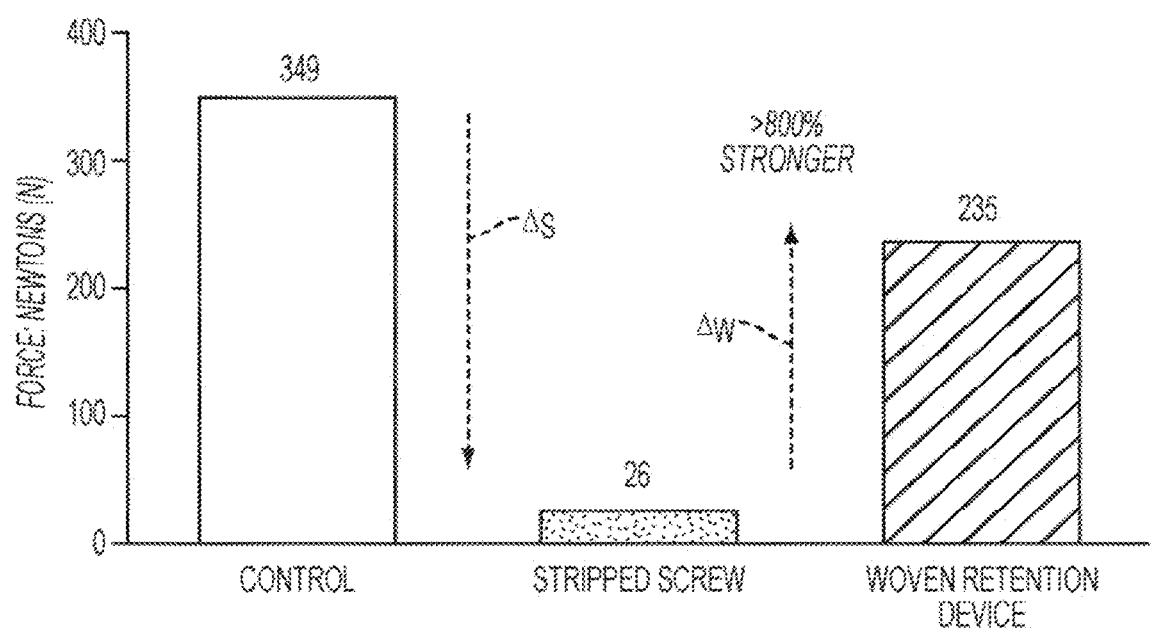
FIG. 5 shows a pullout strength comparison for a screw, a screw in a stripped bone hole, and a woven retention device with screw in a stripped bone hole, according to an example of an embodiment of the present invention.

FIG. 5 shows a graph of examples of pullout strengths of a screw in control bone hole, a screw in a stripped bone hole, and, according to an example of an embodiment of the invention, a screw in a woven retention device in a stripped bone hole. A stripped bone hole is one in which a screw, for one reason or another, has lost purchase or fit. For example, the bone may degrade or break to the point that the fit between the bone and the screw is lost, or part of the structure of the bone may be stripped or sheared by the screw itself, for example. As can be seen from FIG. 5, a screw in a stripped bone hole can cause a decrease AS in the pullout strength of the screw as compared to a control screw that is in a bone hole that is not stripped. In addition, the woven retention device in accordance with the principles of the invention can cause an increase AW in the force required to pullout the screw as compared to the screw by itself in a stripped hole. Although not shown in FIG. 5, the woven retention device can increase the pullout strength of the screw beyond that of a screw in a non-stripped hole, such as the control screw, including in cases where the woven retention device is used in conjunction with a screw in a non-stripped hole.

Figure 6:
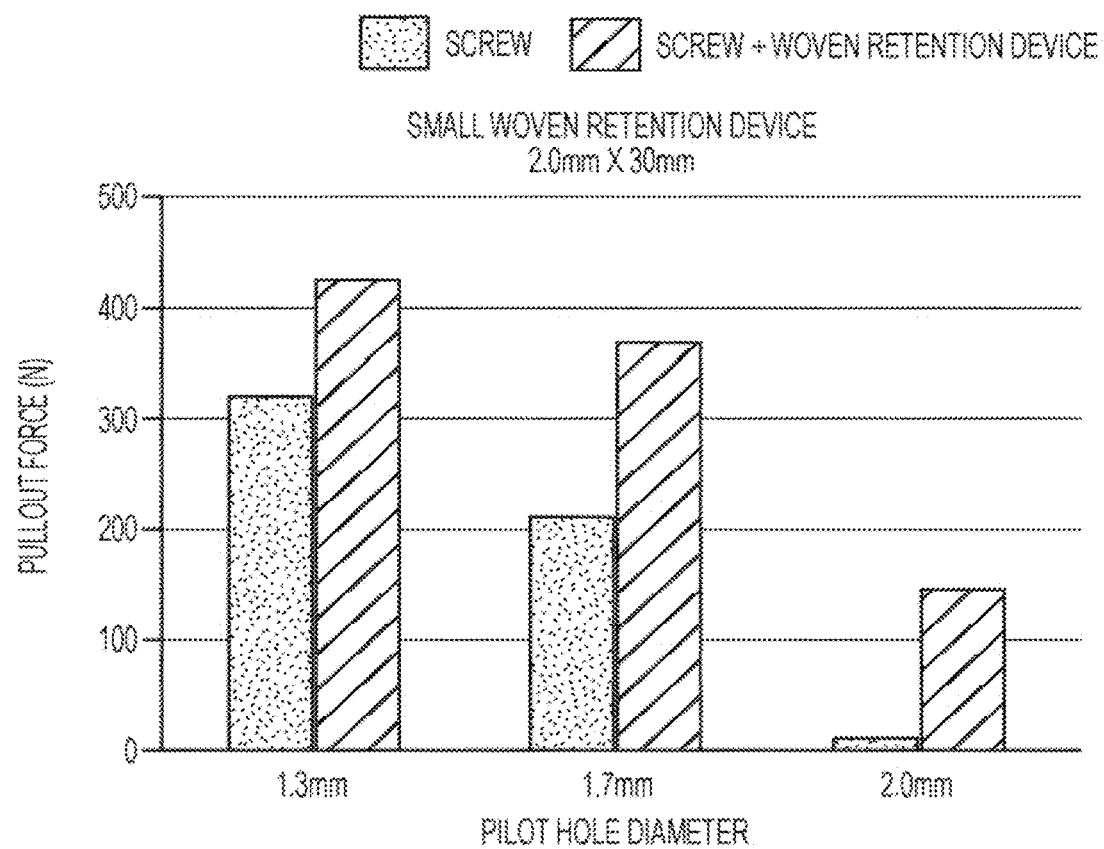
FIG. 6 shows a pullout force versus hole diameter for a screw and a screw with a woven retention device, in accordance with the principles of the present invention.

FIG. 6 shows a graph showing examples of different pullout forces between small screws in various different pilot holes. As can be seen from FIG. 6, the combination of the screw and woven fixation device, in accordance with the principles of the invention, has more pullout force in each of the tested sizes.

Figure 7:
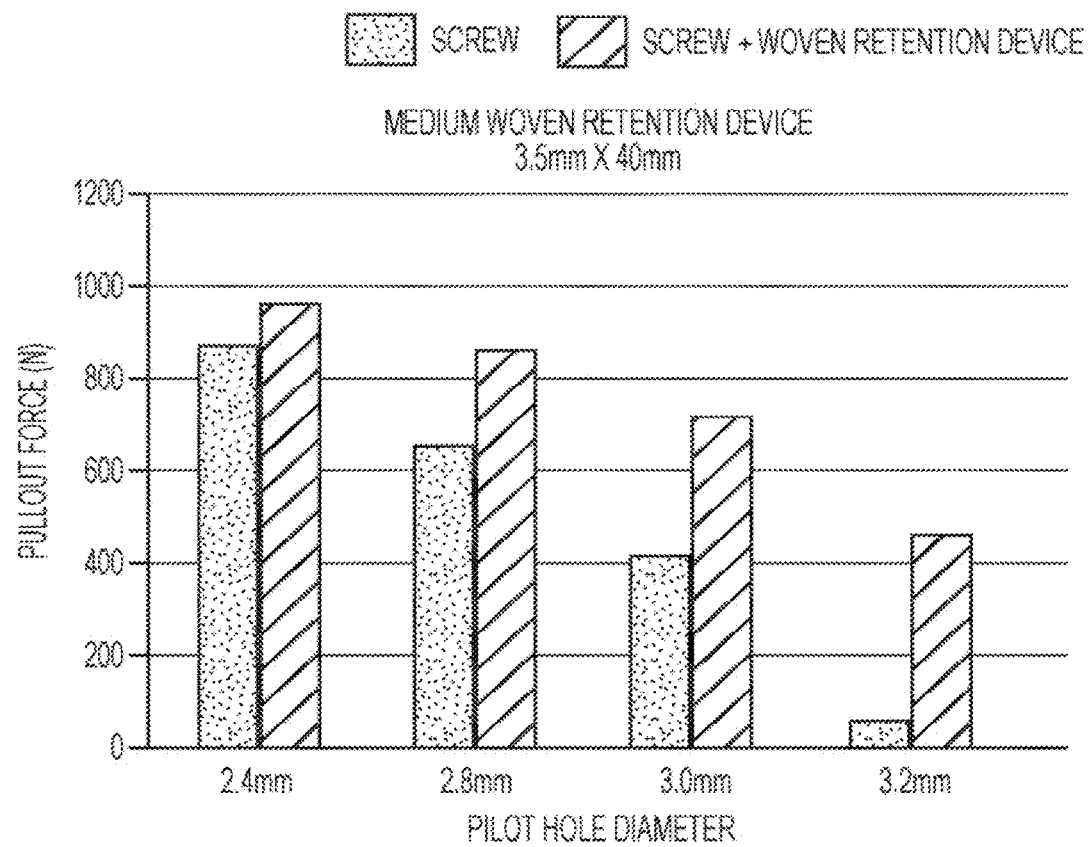
FIG. 7 shows another pullout force versus hole diameter for a screw and a screw with a woven retention device, in accordance with the principles of the present invention.

FIG. 7 shows a graph showing examples of different pullout forces between medium screws in various different pilot holes. As can be seen from FIG. 7, the combination of the screw and woven fixation device, in accordance with the principles of the invention, has more pullout force in each of the tested sizes.

Figure 8:
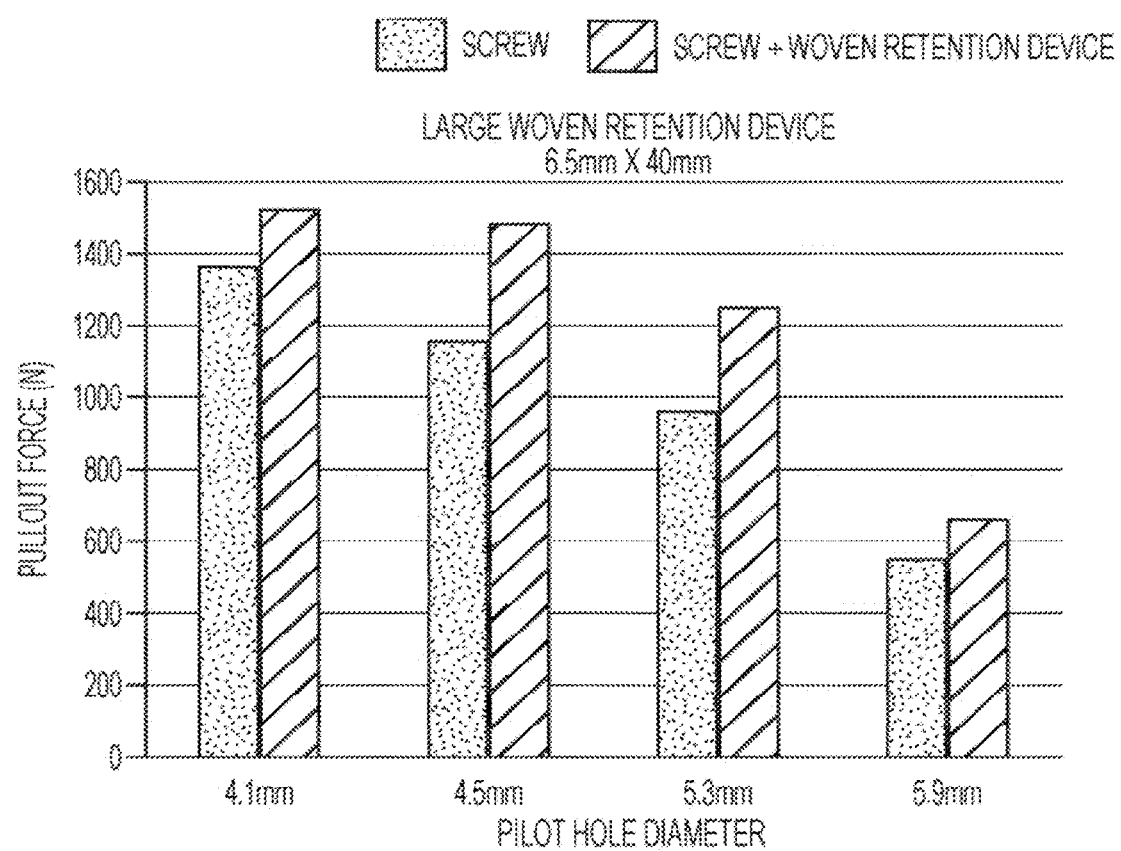
FIG. 8 shows another pullout force versus hole diameter for a screw and a screw with a woven retention device, in accordance with the principles of the present invention.

FIG. 8 shows a graph showing examples of different pullout forces between large screws in various different pilot holes. As can be seen from FIG. 8, the combination of the screw and woven fixation device, in accordance with the principles of the invention, has more pullout force in each of the tested sizes.

FIG. 15 shows an exemplary spine ovine study showing bone growth over 12 weeks with a 4.5 mm screw.

According to embodiments of the invention, the woven retention device can enhance pullout force percentage compared with a screw alone for a range of hole diameters. However, the woven retention device used with a small screw may allow for a higher percentage increase of pullout force than with medium and large screws. For example, the woven retention device according to an embodiment has been shown to add at least a 10% increase in pullout strength compared with the pullout force of a screw without a woven retention device. Specifically, for small hole diameters, the increase has been shown to be 33% to 77%, according to an example of one embodiment. For medium hole diameters, the increase has been shown to be 10% to 72%, according to another example of an embodiment. Finally, for large hole diameters, the increase has been shown to be 12% to 30% according to another example of an embodiment.

Examples of woven retention devices according to embodiments were fabricated using different combinations of filaments. Table 5 shows details of the five versions of these examples. Each version includes two types of counter clockwise filaments, and two types of clockwise filaments. "Type" refers to whether the filament is monofilament or multi-filament. "Size" indicates the diameter (measured in millimeters) of the monofilaments, and the linear mass density (measured in decitex, or dtex, which is grams per 10,000 meters) for the multifilament. "# of Carriers" refers to the number of each filament. Version 1 is a combination of mono- and multifilaments. Version 2 is only monofilaments, where the monofilaments are all the same size. Version 3 is a combination of two different sizes of monofilaments. Version 4 is a combination of three different sizes of monofilaments. The woven retention devices in Versions 1-5 each had a braid angle of about 40° to 45°, and were sized to accommodate screw with an inner core diameter of about 6.5 mm (corresponding to the "large" size discussed above). The filaments were made of polyethylene terephthalate (PET).

TABLE 5

Examples of woven retention devices used for measuring pullout strength

|  | Counter Clockwise Filaments | | | Clockwise Filaments | | |
| --- | --- | --- | --- | --- | --- | --- |
|  | Type | Size | # of Carriers | Type | Size | # of Carriers |
| Version 1 | mono | 0.2 mm | 12 | mono | 0.2 mm | 12 |
|  | multi | flat 196 dtex | 12 | multi | flat 196 dtex | 12 |
| Version 2 | mono | 0.2 mm | 12 | mono | 0.2 mm | 12 |
|  | mono | 0.2 mm | 12 | mono | 0.2 mm | 12 |
| Version 3 | mono | 0.2 mm | 12 | mono | 0.2 mm | 12 |
|  | mono | 0.1 mm | 12 | mono | 0.1 mm | 12 |
| Version 4 | mono | 0.4 mm | 12 | mono | 0.2 mm | 12 |
|  | mono | 0.1 mm | 12 | mono | 0.1 mm | 12 |
| Version 5 | mono | 0.2 mm | 12 | mono | 0.2 | 12 |
|  | mono | 0.3 mm | 12 | mono | 0.3 | 12 |

Figure 9:
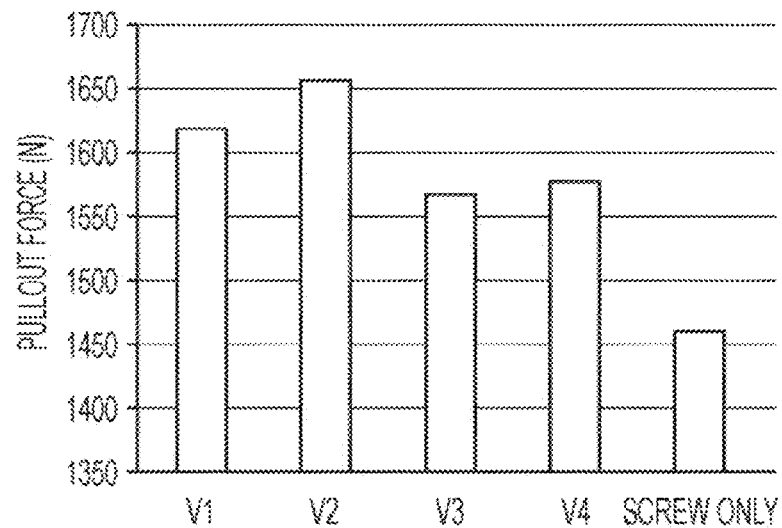
FIG. 9 shows pullout forces measured for woven retention devices of varying construction pulled from a first material, according to examples of embodiments of the present invention.
Figure 10:
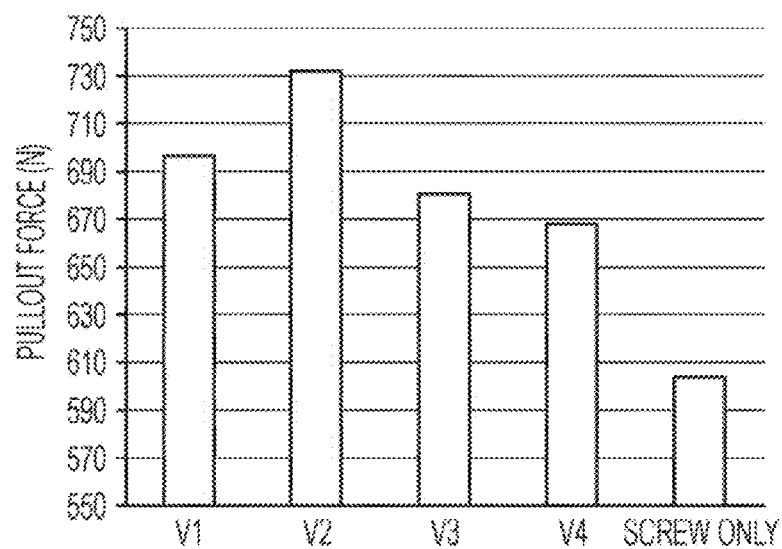
FIG. 10 shows pullout forces measured for woven retention devices of varying construction pulled from a second material, according to examples of embodiments of the present invention.

FIGS. 9 and 10 show the results of axial pullout strength using Versions 1-5 of the woven retention device in Table 5 as compared to the pullout strength of a screw without a woven retention device. Both tests used pilot holes with a diameter of 4.1 mm in polyurethane foam, and a screw with an inner core diameter of 6.5 mm and length of 40 mm. In the tests of FIG. 9, 15 pcf rigid polyurethane foam was used. In the tests of FIG. 10, 10 pcf rigid polyurethane foam was used. For all tests, the axial pullout strength was greater when a woven retention device was used, compared to when a screw was used without a woven retention device. Furthermore, FIGS. 9 and 10 show that the greatest pullout strength in these tests was achieved for Version 2, which comprised only monofilaments of the same size. Also, the percentage increase compared to screw-only pullout was greater in the less dense (10 pcf) polyurethane foam, indicating that embodiments of the present invention may well suited for lower density bone, such as osteoporotic or osteopenic bone, for example.

There is a need for devices, systems and methods that enhance the surface of a bone hole to provide enhanced fixation of a bone anchor to the bone such as is described in copending application Ser. No. 15/374,773, herein incorporated by reference. Additionally, there is a need for devices, systems and methods for repairing the surface of the bone hole following damage to the bone hole as in the case of stripping of the hole in the bone when a bone screw is over-tightened. Also, there is a need for devices, systems and methods for providing an enhanced bone hole surface for the reattachment of tendons in, for example anterior/posterior cruciate ligament repair procedures, rotator cuff repair procedures, etc. There is a need for a device that enhances the surface of a bone hole to enhance fixation of a bone anchor to bone and permits bone ingrowth into its structure. There is a need for a single device that enhances the surface of a bone hole to enhance fixation of a bone anchor to bone and accommodates variations in the diameter and depth of the bone hole. Further, there is a need for such devices that have enhanced biocompatibility to aid in tissue and bone healing, regeneration, and growth.

According to an embodiment of the present invention, a retention device for interfacing with a bone surface and promoting bone ingrowth and impeding biofilm development is provided. The retention device includes a sleeve body including a plurality of filaments forming a substantially tubular lattice with a plurality of protuberances distributed on an interior surface and an exterior surface of the tubular lattice at a predetermined spatial relationship. The sleeve body can surround at least a portion of a fastener, and each of the plurality of protuberances may be formed by an intersection point of two or more of the plurality of filaments that outline a plurality of apertures. The filaments can include an orthopedic biomaterial. The retention device also may include a proximal end that is proximal to the sleeve body and that can receive at least a portion of the fastener, and a distal end that is distal to the sleeve body. In a first state, the sleeve body may have a plurality of combinations of filament cross-section geometries at the intersection points, the plurality of combinations of filament cross-section geometries forming a plurality of protuberance thicknesses. A thickness of each protuberance is measured in a radial direction of the sleeve body. In a second state when a fastener is inserted into the tubular lattice, pressure from the fastener can be transmitted to the tubular lattice such that the spatial relationship of the protuberances changes according to a function of bone density and according to a function of an interfacing surface shape of the fastener.

In an aspect of an embodiment, the retention device can be a woven retention device and the filaments may be interwoven. The orthopedic biomaterial can include a hydrophilic material that attracts bone growth, and the hydrophilic material can be a metal. The orthopedic biomaterial can include non-resorbable polymer fibers. The orthopedic biomaterial can include at least one of osteostimulative, antimicrobial, and plasma-rich-platelet (PRP) agents applied to the filaments. In an embodiment, the non-resorbable polymer fibers are roughened to wick one of osteostimulative, antimicrobial and plasma-rich-platelet agents. The orthopedic biomaterial may include biologic fibers that are configured to absorb into a body, and the non-resorbable polymer fiber and the biologic fibers may be interwoven.

As may be appreciated from the foregoing disclosure, the fundamental requirement for bone growth is the linear distance between obstacles. In the case of a woven retention device, the linear distance is the filament to filament distance, and in particular, the diagonal distance of the 3-dimensional shape (e.g. a parallelepiped). The preferred range for the linear distance between filaments surfaces is greater than 200 μm and smaller than 1000 μm for every pore. This range may be extended to 100 μm to 1100 μm. The target distance may be 600 μm. However, not every pore has to be optimally sized for bone growth since having small gaps that do not allow bone to grow will not adversely impact fixation measurably. Fixation would depend on the surface area covered with bone. For example, if the number of pores that prevent bone growth is less than 10% of the area then the fixation strength would not be affected.

As may further be appreciated, having a pore size which promotes bone formation may impede biofilm formation. Biofilm formation is stimulated by an adverse reaction to a material, like a foreign body response or growth of infection from influx of bacteria etc. Where there is bone formation, there is nothing else, and thus biofilm formation may be impeded. However, there could be normal soft tissue growth instead of biofilm. Normal soft tissue (fibrotic response) can fill in the empty space if there is no promotion of bone growth (e.g. the gap is very large and there is no stress or micromotion to stimulate the bone to respond). Less normal soft tissue growth occurs with the interwoven retention device of the present disclosure since it bridges the gap, transfers load to the bone to stimulate growth, and provides a platform to grow onto.

Furthermore, when the pores are constricted and/or expanded, the pore size still falls within the predetermined range. The shape of the pore (e.g. the parallelepiped) may change, but the overall distance between filaments remains in the predetermined range. The area of the aperture may change dynamically by interwoven filaments translating with respect to each other without substantial stretching of the interwoven filaments. If one constricts or expands the sleeve, first there is translation of fibers then eventually there is stretching or buckling of the fibers. The constricted aperture areas may change by a function of a braid of the filaments. The aperture area (shape of the parallelograms) at rest is determined by the braid. Therefore, the shape of the aperture after compression or expansion is also determined by braid. As previously discussed, the pore size may be defined in other terms and may be the area, length, width, or other dimension of the pore. Any of these parameters may define the pore size since what impacts bone growth is the 3-dimensional distance between surfaces (obstacles) that would prevent growth. If the 3-dimensional distance is too small, the osteoclasts are impeded from creating bone and if the 3-dimensional distance is too large, the osteoclasts are not constrained and will not form bone. The braid parameters that create the protuberances for increased fixation can also create a pore size for optimal bone growth. The braid of the sleeve that creates asymmetrical protuberances for 3-D interdigitation for fixation also create asymmetrical pores for 3-D optimal bone growth. The pore size may stay in a range that is optimal for bone growth regardless of the diameter of the sleeve when compressed or expanded.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A retention device to promote bone ingrowth and impede biofilm formation, the retention device comprising:
a sleeve body comprising a plurality of filaments, the sleeve body having an exterior surface and an interior surface, wherein the exterior surface is configured to contact a bone surface, and wherein the interior surface is configured to contact a fastener;
a proximal end that is proximal to the sleeve body and that is configured to receive the fastener; and
a distal end that is distal to the sleeve body on an opposing side of the proximal end,
wherein the retention device is configured to have a relaxed state and a constricted state,
wherein in the relaxed state of the retention device, the plurality of filaments outline a plurality of pores, each of the pores having a pore size along a plane of the plurality of filaments, each pore size within a range of 400-800 µm,
wherein in the constricted state of the retention device, the pore size changes as a function of a diameter of the retention device, the pore size remaining within the range of 400-800 µm, wherein the diameter of the retention device in the relaxed state is different than the diameter of the retention device in the constricted state,
wherein the pores are configured to promote bone ingrowth and impede biofilm formation, and
wherein the plurality of filaments comprises at least one filament with a diameter between 0.2 mm and 0.4 mm.

2. The retention device of claim 1, wherein an area of the pores changes dynamically by filaments translating with respect to each other without substantial deforming of the filaments.

3. The retention device of claim 2, wherein the area of the pores changes by a function of a braid of the filaments.

4. The retention device of claim 3, wherein the pore size is defined along a long axis or a major axis of the sleeve body.

5. The retention device of claim 4, wherein the filaments define a plurality of protuberances distributed on the interior surface and the exterior surface of the sleeve body at a predetermined spatial relationship.

6. The retention device of claim 5, wherein in the relaxed state each pore is shaped as one of a diamond, a rectangle, a square, or a parallelogram.

7. The retention device of claim 1, wherein the plurality of filaments comprise at least one 0.3 mm diameter filament, and at least one 0.2 mm diameter filament.

8. The retention device of claim 1, wherein the plurality of filaments comprise at least one 0.2 mm diameter filament, and at least one 0.1 mm diameter filament.

9. The retention device of claim 1, wherein the plurality of filaments comprise at least one 0.1 mm diameter filament, at least one 0.2 mm diameter filament, and at least one 0.4 mm diameter filament.

10. The retention device of claim 1, wherein the retention device is a woven retention device.

11. The retention device of claim 1, wherein the plurality of filaments are interwoven.

12. The retention device of claim 1, wherein the retention device is formed from a non-bioabsorbable material.

13. A retention device comprising:
a sleeve body comprising a plurality of filaments, the sleeve body having an exterior surface and an interior surface, wherein the exterior surface is configured to contact a bone surface, and wherein the interior surface is configured to contact a fastener;
a proximal end that is proximal to the sleeve body and that is configured to receive the fastener; and
a distal end that is distal to the sleeve body on an opposing side of the proximal end,
wherein the retention device is configured to have a relaxed state and a constricted state,
wherein in the relaxed state of the retention device, the plurality of filaments outline a plurality of pores, each of the pores having a pore size along a plane of the plurality of filaments, each pore size within a range of 400-800 µm,
wherein in the constricted state of the retention device, the pore size changes as a function of a diameter of the retention device, the pore size remaining within the range of 400-800 µm, wherein the diameter of the retention device in the relaxed state is different than the diameter of the retention device in the constricted state, and
wherein the plurality of filaments comprises at least one filament with a diameter between 0.2 mm and 0.4 mm.

14. A retention device to promote bone growth, the retention device comprising:
a sleeve body comprising a plurality of filaments that form a substantially tubular lattice having a plurality of pores having a predetermined pore size, the plurality of pores defined by a plurality of adjacent filaments of the plurality of filaments, wherein the substantially tubular lattice comprises an exterior surface and an interior surface, wherein the exterior surface is configured to contact a bone surface, and wherein the interior surface is configured to contact a fastener, wherein the retention device is configured to move between a relaxed state and a constricted state, wherein the predetermined pore size falls within a predetermined range and remains substantially within the predetermined range when the retention device is in the relaxed state and the constricted state, wherein a diameter of the retention device in the relaxed state is different than the diameter of the retention device in the constricted state, wherein the predetermined pore size is within a range of 200 µm and 600 µm, wherein the predetermined pore size promotes bone growth in the pores, and wherein the plurality of filaments comprises at least one filament with a diameter between 0.2 mm and 0.4 mm.

15. The retention device of claim 14, wherein the predetermined pore size is defined by a 3-dimensional distance between surfaces of the plurality of adjacent filaments.

16. The retention device of claim 14, wherein the pores define a parallelepiped between the plurality of adjacent filaments.

17. The retention device of claim 14, wherein a 3-dimensional distance between surfaces of the plurality of adjacent filaments is a length between opposing diagonal corners of the pores.

18. The retention device of claim 14, wherein the predetermined pore size is defined when the retention device is in the relaxed state.

19. The retention device of claim 14, further comprising a plurality of protuberances distributed on the interior surface and the exterior surface of the substantially tubular lattice at a predetermined spatial relationship.

20. The retention device of claim 14, wherein the predetermined pore size is defined along a long axis or a major axis of the sleeve body.

21. The retention device of claim 14, wherein the predetermined pore size remains in the range of 200 µm and 600 µm when a diameter of the retention device changes.

* * * * *